(12) United States Patent
Shah

(10) Patent No.: US 11,007,203 B2
(45) Date of Patent: May 18, 2021

(54) FORMULATIONS COMPRISING ALDOSTERONE RECEPTOR ANTAGONISTS AND TREATMENTS USING SAME

(71) Applicant: Salim Shah, Vienna, VA (US)

(72) Inventor: Salim Shah, Vienna, VA (US)

(*) Notice: Subject to any disclaimer, the term of this patent is extended or adjusted under 35 U.S.C. 154(b) by 0 days.

(21) Appl. No.: 16/786,813

(22) Filed: Feb. 10, 2020

(65) Prior Publication Data

US 2020/0171054 A1 Jun. 4, 2020

Related U.S. Application Data

(63) Continuation-in-part of application No. 16/247,555, filed on Jan. 14, 2019, now Pat. No. 10,596,119, which is a continuation-in-part of application No. 16/184,575, filed on Nov. 8, 2018, now Pat. No. 10,463,622, which is a continuation-in-part of application No. 15/027,355, filed as application No. PCT/US2013/077732 on Dec. 26, 2013, now Pat. No. 10,154,963.

(60) Provisional application No. 61/887,396, filed on Oct. 6, 2013.

(51) Int. Cl.
*A61K 31/585* (2006.01)
*A61K 9/16* (2006.01)

(52) U.S. Cl.
CPC .......... *A61K 31/585* (2013.01); *A61K 9/1623* (2013.01); *A61K 9/1652* (2013.01)

(58) Field of Classification Search
None
See application file for complete search history.

(56) References Cited

U.S. PATENT DOCUMENTS 6,410,054 B1 * 6/2002 Thosar ................. A61K 9/4866
424/489
2002/0132001 A1 * 9/2002 Garthwaite ............... A61P 9/04
424/468

OTHER PUBLICATIONS

Landin et al. (Comparison of two Varieties of Microcrystalline Cellulose as Filler Binders II. Hydrochlorothiazide Tablets, Drug Development and Industrial Pharmacy, vol. 19, 1993 Issue 10). (Year: 1993).*

* cited by examiner

*Primary Examiner* — Melissa S Mercier
(74) *Attorney, Agent, or Firm* — US IP Attorneys, P.C.; Timothy Marc Shropshire

(57) ABSTRACT

Disclosed herein are oral dose formulations of aldosterone receptor antagonists, such as eplerenone and spironolactone, for the treatment of heart failure with preserved ejection fraction and uncontrolled hypertension.

9 Claims, 6 Drawing Sheets

FORMULATIONS COMPRISING ALDOSTERONE RECEPTOR ANTAGONISTS AND TREATMENTS USING SAME

CROSS-REFERENCE TO RELATED APPLICATION(S)

The present application is a continuation-in-part of application Ser. No. 16/247,555 filed on Jan. 14, 2019, entitled "Methods of Treatment Comprising Torsemide", the entire disclosure of which is incorporated by reference herein.

FIELD OF THE INVENTION

The invention is directed to controlled-release (CR) (e.g., extended-release (ER), prolonged-release (PR), or sustained release (SR)) oral dosage formulation comprising an effective amount of Torsemide and/or an aldosterone receptor antagonist (e.g., spironolactone or eplerenone), or a pharmaceutically acceptable salt of one or both of the foregoing, and at least one controlled-release excipient.

BACKGROUND OF THE INVENTION

Congestive heart failure (CHF) affects 1.7% of the US population, 4.6 million people have chronic heart failure, there are 550,000 new cases per annum and approximately 60% are over 70 years of age. The etiological causative factors are coronary heart disease, hypertension, cardiac valvular disease, arrhythmias, cardiomyopathy and diabetes. It is associated with high mortality. In the US the median survival following onset of CHF is 1.7 years in men and 3.2 years in women. Data generated from Scotland shows a 3-year mortality rate after first hospitalization for CHF patients' age 65 years and older is approximately 66%.

Diuretics play an essential role in modern cardiovascular therapy, and are currently recommended for the treatment of CHF. Diuretics suffer from many defects or complications including electrolyte and metabolic disturbances and reduction in glomerular filtration rate (GFR). The GFR is already reduced in most patients with edematous conditions and declines further over time eventually mandating the use of loop diuretics since these agents have the most potent acute pharmacological action of natriuresis and diuresis. However, any further fall in GFR will compromise the fluid and salt depleting actions of the diuretic and may lead to a "cardio-renal syndrome." Prior studies with furosemide in normal subjects consuming a high salt intake showed that furosemide increased the GFR immediately after the dose, but reduced it thereafter by circa 23% during the remainder of the day.

Despite their unrivaled acute effectiveness, loop diuretics have been disappointing therapeutic agents. They cause little or no reduction in blood pressure (BP) in hypertensives, resulting in a preference for less acutely natriuretic and diuretic drugs such as thiazides or mineralocorticoid receptor antagonists (MRAs, aka aldosterone receptor antagonists). Furosemide's short half-life and extreme variation in bioavailability may account for its unpredictable effects in treating patients with CHF and bumetanide is even more short acting.

A class defect of loop diuretics is their short duration of action of 2-4 hours even after oral dosing. Two problems may ensue. First, the plasma concentration of the loop diuretic resides within the "most efficient" 25% to 75% of maximum level for less than one hour. Second, their abrupt action leaves about 20 hours for the kidney to regain the salt and water lost before the next daily dose. This accounted for the failure of furosemides or bumetanide to cause net $Na^+$ loss over 1-3 days of once daily administration to normal subjects unless dietary salt was restricted.

Torsemide has been developed as a newer type of loop diuretic with a longer half-life, longer duration of action, and higher bioavailability compared to the most commonly used loop diuretic, furosemide.

Torsemide is routinely used for the treatment of both acute and chronic CHF and arterial hypertension (AH). Torsemide is similar to other loop diuretics in terms of its mechanism of diuretic action. It has higher bioavailability (about 80%) and a longer elimination half-life (3 to 4 hours) than furosemide. In the treatment of CHF Torsemide (5 to 20 mg/day) has been shown to be an effective diuretic. Non-diuretic dosages (2.5 to 5 mg/day) of Torsemide have been used to treat essential AH, both as monotherapy and in combination with other antihypertensive agents (e.g. calcium channel blocker, ACE inhibitors, ARBs, diuretics, and alpha and/or beta blockers). When used in these dosages, Torsemide lowers diastolic blood pressure to below 90 mm Hg in 70 to 80% of patients. Antihypertensive efficacy of Torsemide is similar to that of thiazides and related compounds. Thus low-dose Torsemide constitutes an alternative to thiazides diuretics in the treatment of essential AH.

Torsemide also appears to have additional actions beyond a pure diuretic effect, such as an anti-aldosterone effect and vaso-relaxation effect. These effects of Torsemide are mediated via several biological pathways including but not limited to modulation of renin-angiotensin-aldosterone system (RAAS), modulation of guanylyl cyclase activity, modulation of secretion of brain natriuretic peptide and atrial natriuretic factor, modulation of mineralocorticoid receptors, collagen/collagen type I, and myocardial fibrosis. All of these effects of Torsemide are dependent and concentration and duration of Torsemide bioavailability. The extended release Torsemide formulations described here maintain Torsemide bioavailability for longer duration as compared to the immediate release Torsemide and thereby differentially modulate above biological pathways. Moreover, studies have also investigated whether the superior pharmacokinetics and pharmacological activity of Torsemide result in a favorable clinical outcome. Their results have indicated that, in comparison with furosemide, Torsemide improves left ventricular function, reduces mortality as well as the frequency and duration of heart failure-related hospitalization, and improves quality of life, exercise tolerance and NYHA functional class in patients with congestive heart failure. Thus, Torsemide appears to be a promising loop diuretic that contributes to better management of patients with heart failure.

Torsemide is a high-ceiling loop diuretic, which acts on the thick ascending limb of the loop of Henle to promote rapid and marked excretion of water, sodium and chloride. Like furosemide, its major site of action is from the luminal side of the cell. Torsemide is at least twice as potent as furosemide on a weight-for-weight basis, produces equivalent diuresis and natriuresis at lower urinary concentrations and has a longer duration of action, allowing once-daily administration without the paradoxical antidiuresis seen with furosemide. Torsemide also appears to promote excretion of potassium and calcium to a lesser extent than furosemide. In trials of up to 48-week duration in patients with mild to moderate essential hypertension, Torsemide, administered as a single daily dose, has been shown to achieve adequate blood pressure control reaching steady-state within 8 to 12 weeks. Those patients not responding initially have generally responded to a doubling of the dose. Comparative trials of up to 6 months show Torsemide is as effective as indapamide, hydrochlorothiazide or a combination of triamterene/hydrochlorothiazide in maintaining control of blood pressure. Torsemide has also been used successfully to treat edematous states associated with chronic congestive heart failure, renal disease and hepatic cirrhosis. In short term trials control of blood pressure, bodyweight and residual edema has been sustained. Torsemide appears to be a useful alternative to furosemide in these patients, providing potent and long-lasting diuresis while being relatively potassium and calcium sparing. In clinical trials to date Torsemide has been well tolerated with adverse effects of a mild, transient nature reported by only small numbers of patients. Changes in biochemical parameters have been common, including decreases in plasma sodium and potassium levels and increases in plasma creatinine and uric acid levels. These changes are typical of loop diuretics. No changes were clinically significant nor were clinically relevant changes noted in glucose metabolism, cholesterol or triglyceride levels or in hematological values. Thus, Torsemide is an interesting new loop diuretic with potential use in the treatment of mild to moderate essential hypertension and of edematous states in which diuretic therapy is warranted. Preliminary studies suggest it to be as efficacious as other diuretics in common use and to have some advantage over furosemide in duration of action and in effects on potassium and calcium.

CHF is the cause of significant mortality all over the world and its incidence and prevalence are increasing. Fluid retention and volume overload are responsible in large part of morbidity related to heart failure. Torsemide is the only loop diuretic for which it has been shown to effectively lower high blood pressure even with low doses. In addition, Torsemide is a very safe drug. In a post marketing surveillance study (TORIC) of 1,377 patients with CHF, Torsemide significantly reduced cardiovascular mortality in comparison to furosemide; see Ishido et al., Torsemide for the treatment of heart failure. *Cardiovasc. Hematol. Disord. Drug Targets.* 2008 June; 8(2):127-32. Review, herein incorporated by reference in its entirety. In a recent study, Torsemide reversed myocardial fibrosis and reduced collagen type I synthesis, improving cardiac remodeling in patients with CHF; see Preobrazhenskii et al., Torsemide is the effective loop diuretic for long-term therapy of arterial hypertension. *Kardiologiia.* 2011; 51(4):67-73. Review, herein incorporated by reference in its entirety.

Hypertension is among the most prevalent chronic diseases, affecting 29% of the US population. Sodium retention with associated fluid retention/fluid overload commonly contributes to hypertension in adults. Consequently, diuretics, in particularly thiazide diuretics, are indicated as first line therapy for hypertension in adults. Although hypertension is also common in children, affecting anywhere from 3% to up to 16%, children with hypertension are less likely to manifest hypertension-associated fluid overload and edema. Etiologies of hypertension in children and adolescents are varied and include primary/idiopathic hypertension which is the most common cause accounting for approximately 90% of all cases, renal, cardiovascular diseases including coarctation of the aorta, endocrine, environmental exposures (e.g. lead, cadmium, mercury and phthalates), neurofribromatosis, and iatrogenic or medication-related[6]. Obesity is strongly associated with primary hypertension in children and adolescents and is believed to be a significant contributor to increasing rates of hypertension in the pediatric population.

Adults and children with intravascular volume overload and edema are routinely treated with diuretic therapy. Diuretics are recommended by the joint ACC/AHA/HFSA guidelines for the relief of symptoms due to volume overload in patients with heart failure with preserved ejection fraction. Loop diuretics are the mainstay of therapy for edema and fluid overload following cardiac surgery in adults and children. Furosemide, torsemide and bumetanide are the most commonly used diuretics in pediatrics, and most children are exposed to either drug during their recovery from cardiac surgery. Diuretics are also recommended by the joint ACC/AHA/AAPA/ACPM/AGS/APhA/ASH/ASPC/NMA/PCNA guidelines for primary treatment of hypertension in adults. Thiazide diuretics are recommended as first line agents and aldosterone receptor antagonists as well as loop diuretics are also recommended in select clinical scenarios. Recommended first line drug therapies for treatment of hypertension in children and adolescents include angiotensin converting enzyme (ACE) inhibitors, angiotensin receptor blockers (ARBs), calcium channel blockers (CCBs) and/or thiazide diuretics. Current guidelines do not include loop diuretics as first line therapy and loop diuretics are very rarely used for the treatment of hypertension in the pediatric population.

Unfortunately, adverse events including electrolyte imbalance and rapid changes in intravascular fluid status resulting from rapid and excessive, but brief diuresis are common with use of any diuretics. Children after cardiac surgery are particularly vulnerable to both electrolyte imbalances and to the resulting risk of arrhythmias, and intravascular volume depletion and the risk of hypotension.

Loop diuretics are also routinely used as supportive therapy to treat volume overload and edema resulting from acute or chronic presentations of renal diseases. Loop diuretics are recommended as the mainstay of treatment for nephrotic edema by the KDIGO Clinical Practice Guidelines for Glomerulonephritis for both adults and children on the basis of several retrospective and prospective clinical studies demonstrating improved diuresis, natriuresis, or reduction in body weight.

Diuretics are also used in cases of severe volume overload secondary to acute or chronic liver failure, though risks of excessive intravascular volume depletion must be carefully considered. In this population, co-administration of diuretics with intravenous albumin infusion may be considered to protect the intravascular volume and avoid worsening hepatic encephalopathy and other complications. Loop diuretics are endorsed in several American Association for the Study of Liver Diseases (AASLD) practice guidelines including the treatment of ascites due to cirrhosis, and the initial evaluation and management of adults and children presenting for liver transplantation.

Of the four main loop diuretics available in the United States (furosemide, bumetanide, ethacrynic acid, torsemide IR), furosemide is the most commonly used in children. To date only a single prospective, non-randomized clinical trial published in 2008 from Japan studied the efficacy and safety of torsemide IR (Demadex) in children. A total of 102 children ages 3 weeks to 5 years with either newly diagnosed heart failure or previously diagnosed heart failure received de-novo treatment with torsemide IR (Demadex) or were switched from prior furosemide therapy (of >3 months duration) to torsemide. In most children, heart failure resulted from structural congenital heart defects, most commonly ventricular septal defects, while dilated cardiomyopathy was diagnosed in only 6 children. Children were excluded if they: (i) were <2 weeks old; (ii) had undergone surgery in the 4 weeks prior to enrollment; or (iii) suffered from acute decompensated heart failure at the time of enrollment. Torsemide IR (Demadex) dosing ranged from 0.18 to 0.8 mg/kg. The efficacy of torsemide IR (Demadex) was evaluated for its effects on clinical signs and symptoms of heart failure using a modified New York University Pediatric Heart Failure Index, diuretic effect, effects on humoral activation (plasma concentrations of brain natriuretic peptide, renin activity, and serum concentrations of aldosterone), and potassium sparing effect at 3-4 weeks follow up. In the de-novo group, torsemide IR (Demadex) initiation improved the heart failure score, decreased serum brain natriuretic peptide concentrations, and reduced echocardiographically measured end-systolic and end-diastolic dimensions of the left ventricle, while improving fractional shortening. In a subset of 6 children hospitalized while transitioned from furosemide to torsemide IR (Demadex) therapy, mean urine output increased while treated with torsemide IR (Demadex). There were no reports of adverse events necessitating drug discontinuation, and electrolyte imbalances were uncommon, suggesting that the drug is relatively safe in children.

Despite their frequent use in both adults and children, a common limitation of the four main loop diuretics (furosemide, bumetanide, ethacrynic acid, and torsemide IR) is the relatively short duration of action of approximately 2-4 hours. Unless repeatedly dosed over a 24-hour period, this limited duration of action leaves significant time for the kidney to regain salt and water lost during diuresis, negating the net effects of diuretic therapy. An extended release torsemide formulation is an attractive strategy to prolong duration of action thereby preserving net diuretic effects even with once daily dosing.

The most convenient and commonly employed oral drug formats are solids, such as tablets and capsules. Torsemide is no exception. Many children and some adults however have difficulty swallowing solid dosage formats. To address this problem, torsemide is developed in liquid formulation, either as syrup or suspension.

Drugs are formulated as suspensions for different reasons, but the most common one is poor drug solubility. However, suspensions often require taste masking, specially, drug with poor taste resulting from dissolution in solution. A suspension, however, unlike syrup in which the drug is fully dissolved, requires adequate shaking of the container to resuspend the drug uniformly before dosing. Difficult redispersion of the drug from a sediment, or in the worst case, from caking, will result in under- and over-dosing. This problem of variable dosing is also encountered when the patient or the caregiver forgets to shake the container before dosing. It is therefore desirable to produce a loop diuretic such torsemide, furosemide or bumetanide; or a mineralocorticoid receptor antagonist such as spironolactone or eplerenone in a suspension or in solution form that drug homogeneity is maintained on storage, especially prolonged storage without shaking.

Oral liquid solutions are developed for drug that show almost complete dissolution in an aqueous buffer system; whereas, suspensions are often developed for drugs that are mostly insoluble in aqueous buffer systems. Furthermore, sedimentation of drug particles (drug api or api plus excipient granules) depends on liquid phase viscosity and suspended particle size (i.e., size of drug granules or drug particle size). If the densities of the suspended particle and the liquid phase are the same, sedimentation will not occur. However, precise matching of the densities is difficult. The drug density may be too high, or the amount of density increasing ingredients may be too great. Viscosity of liquid phase can be adjusted by suspending agents such as carbohydrates (e.g., sucrose or other carbohydrate molecules or polymers, including artificial sweeteners and/or synthetic polymers).

In a landmark trial, Pitt et al. reported that patients with heart failure (HF) and reduced ejection fraction (HFrEF) randomized to receive spironolactone (vs. placebo) had a remarkable reduction in mortality and improved clinical outcome.

Since angiotensin II (Ang II) is known to stimulate the release aldosterone, the results of the trial were unexpected because the benefits of spironolactone were seen in patients with HFrEF regardless of whether they were receiving drugs that reduce Ang II effects such as angiotensin converting enzyme inhibitors (ACEis), or angiotensin receptor blockers (ARBs). Consequently, spironolactone has joined a long and growing number of drugs recommended for the treatment of HFrEF.

However, many patients suffer from heart failure with preserved ejection fraction (HFpEF). They experience similar symptoms as those with HFrEF and a similarly impaired quality of life and life expectancy. However, no trials have reported clear benefit in patients with HFpEF. There remain no specific recommendations for its management.

The TOPCAT trial of spironolactone added on to usual therapy for patients with HFpEF did not achieve a significant reduction in primary endpoints. However, it was noted that almost half of the patients were recruited from Russia and the Republic of Georgia. These patients were clearly less severely compromised and derived no benefit from spironolactone. It was apparent that patients from Russia/Georgia had a placebo event rate that was not compatible with prior epidemiological or randomized studies of patients with HFpEF. Many patients from Russia/Georgia assigned to and said to be taking spironolactone did not have evidence of the metabolite of spironolactone, canrenone. Thus, it was not surprising that patients from Russia/Georgia had no significant treatment affects in contrast to those from the Americas. In contrast, patients randomized from the Americas derived a significant reduction in the primary outcome, cardiovascular death and hospitalization for heart failure. Amongst those studied in the Americas, there was a significant increase in hyperkalemia and a doubling of serum creatinine (Scr) for those on spironolactone. However, no significant change in these parameters were observed in the patients randomized to spironolactone from Russia/Georgia. It was concluded that the two populations were quite distinct, both in entry characteristics and in outcomes, although the reasons for these were not clearly established.

The TOPCAT trial was conducted using 15, 30 or 45 mg of the spironolactone; whereas, currently available doses of spironolactone are 25 mg and 50 mg. In the Americas group of the TOPCAT trial, the mean daily dose of spironolactone at four months was 23.8 mg with 25.2% of patients discontinuing the study drug due to hyperkalemia. At four months, patients of the Americas group, randomized to spironolactone, 22% were receiving 15 mg, 42% were receiving 30 mg, and 18% were receiving 45 mg spironolactone.

A population of the Americas patients with HFpEF derived substantial benefits including a significant reduction in all-cause mortality. This has generated interest in providing spironolactone therapy in the US for patients with HFpEF on the basis of experience from the TOPCAT trial. However, there remains no manufacturer or source of spironolactone in the doses used in the TOPCAT (15, 30 and 45 mg) trial. Moreover, there are no data on product manufacturing nor on the pharmacokinetics (PK) parameters of the spironolactone tablets used in the TOPCAT trial. To address this, 15 mg spironolactone tablets were manufactured to establish that the tablets are effective and match, as far as possible, the effects on serum potassium levels as observed in the TOPCAT trial.

Pitt et al. reported results of a pilot trial prior to RALES that assessed responses of patients with HF to placebo or 12.5, 25, 50 or 75 mg daily dose of spironolactone for 12 weeks. Of several parameters measured, the one most closely related to the dose of spironolactone was serum potassium concentration (Sk). The Sk rose dose-dependently with an apparent maximum at 50-75 mg (p<0.001). These were highly significant (p<0.001) dose-dependent effect of spironolactone on Sk at 9 days, 1, 2 and 3 months of the treatment. In the pilot study, spironolactone was added to existing therapy (82% on ACEI and almost all on a diuretic). Likewise, spironolactone was added to similar existing therapy in the TOPCAT trial.

More than 20 million people in the U.S. have Chronic Kidney Disease (CKD). Over half a million people are treated annually for End-Stage Renal Disease (ESRD). In patients with advanced renal failure, high doses of loop diuretics are required to promote negative sodium and water balance and to treat hypertension. Torsemide is a new loop diuretic that has a high bioavailability of 80% and a plasma half-life of 3-5 hours, which remains unchanged in chronic renal failure. Even in patients with advanced renal failure, intravenous and oral high-dose Torsemide proves effective in increasing fluid and sodium excretion in a dose-dependent manner. A number of studies in renal failure patients provide evidence that, on a weight-by-weight basis, the ratio of diuretic potency between Torsemide and furosemide is 1:2.5 after oral dosing and 1:1 after intravenous administration.

However, common problems with diuretics are acute and chronic tolerance. Acute tolerance occurs in a breaking phenomenon associated with a shift to the right of the dose response curve and occurs after initial dosing. Chronic tolerance occurs after 5-10 weeks of dosing and is associated with tubular hypertrophy and sodium rebound phenomena. Although multiple physiological mechanisms are involved in this phenomenon, acute volume depletion is the main stimulus to this phenomenon.

Oral controlled-release (CR) (e.g., extended-release (ER) or prolonged-release (PR)) formulations overcome many of the drawbacks of conventional immediate release (IR) dosage forms.

For example, FIG. 1 shows observed and model-predicted plasma concentration of Torsemide after administration of a 20 mg immediate-release (IR) formulation. As can be seen, the plasma concentration peaks within 1 hour of administration and the concentration decreases thereafter. This may lead to alternating periods of toxic levels and sub-therapeutic concentrations, and thereby decreasing the therapeutic efficacy and inviting toxic side effects.

Contrary to IR dosage forms, CR tablets are not associated with alternating periods of toxic levels and sub-therapeutic concentrations, and thereby improving the therapeutic efficacy and avoiding toxic side effects. Therefore, CR has certain distinct advantages such as (1) reduction in drug plasma level fluctuation with maintenance of a steady plasma level of the drug over a prolonged time period, ideally simulating an intravenous infusion of a drug; (2) reduction in adverse side effects and improvement in tolerability, as drug plasma levels are maintained within a narrow window with no sharp peaks and with AUC of plasma concentration versus time curve comparable with total AUC from multiple dosing with immediate release dosage forms; (3) patient comfort and compliance, as oral drug delivery is the most common and convenient for patients, and a reduction in dosing frequency enhances compliance; (4) reduction in healthcare cost, as the total cost of therapy of the controlled release product could be comparable or lower than the immediate release product. With reduction in side effects, the overall expense in disease management also would be reduced, this greatly reduces the possibility of side effects, as the scale of side effects increase as we approach the maximum safe concentration; and (5) avoid night time dosing, as it is also good for patients to avoid the dosing at night time.

Controlled release products can be classified as follows: (1) reservoir systems including enteric coated products; (2) osmotic systems; (3) ion-exchange resins; and (4) matrix systems. Matrix systems can further be subdivided into (a) monolithic matrix tablets; (b) erodible (hydrophobic) matrix tablets; and (c) gel forming hydrophilic matric tablets Most monolithic matrix tablets use inert matrix, which does not interact (inert) with biological fluids. The main reason for popularity of this system is drug release from the matrix is independent of the states and condition of digestive juices, which shows quite large inter- and intra-patients variability. Nowadays, research in this area focuses on natural biopolymers such as cellulose and starch derivatives, some of which could be considered semi-inert (e.g. ethylcellulose).

Gel-forming hydrophilic or swellable matrix systems are homogeneous or heterogeneous systems in which the drug is dispersed in a swellable hydrophilic polymer. The drug release is a function of polymer characteristics. Most widely studies gel-forming polymer in controlled release is poly (hydroxyethyl methacrylate (pHEMA). Because of their swelling capacity, several cellulose derivatives are applied as swelling gel-forming controlled release drug delivery excipients and most widely used is hydroxypropylmethylcellulose (HPMC). However, a variety of different molecular weight HPMC are available and they vary in their release characteristics. Specifically, viscosity and erosion/dissolution characteristic of gel layer varies greatly and allows manipulations with expected drug released profile.

Other swellable polymers used in matrix tablets are natural or artificial gum, and dextrans. Erodible polymers such as polyanhydrides provide for other types of excipients for controlled release drug with zero-order profile.

U.S. Patent Publication No. 2003/0152622 A1, herein incorporated by reference in its entirety, describes formulations of an erodible gastric retentive oral diuretic, and exemplifies furosemide as the diuretic.

U.S. Patent Publication No. 2007/0196482 A1, herein incorporated by reference in its entirety, describes a sustained release oral dosage form using gum-based gelling gum such as xanthan and locust bean gums.

Moreover, a group in Spain has developed a prolonged-release (PR) Torsemide; see Diez et al., TORAFIC study protocol: Torsemide prolonged release versus furosemide in patients with chronic heart failure. *Expert Rev Cardiovasc Ther.* 2009 August; 7(8):897-904, herein incorporated by reference in its entirety.

Biologically, PR Torsemide was found to be similar in systemic exposure but significantly slower rates of absorption and lower fluctuations in plasma concentrations. Its natriuretic efficiency is higher and diuresis is more constant, with a better tolerability.

However, both the controlled release drug claimed in 2003/0152622-A1 and 2007/0196482-A1 applications, both herein incorporated by reference in their entireties, failed to achieve desired effect sin clinical developments. Additionally, the Spanish version of PR Torsemide shows only a modest release profile of about 5-6 hours.

Therefore, in view of the above, there exists a need in the art for improving the effectiveness of diuretic therapy via better-sustained (e.g., extended) release loop diuretic such as Torsemide.

SUMMARY OF THE INVENTION

In an aspect, the invention provides an extended-release oral dosage formulation, such as a tablet, comprising a therapeutically effective amount of Torsemide and/or an aldosterone receptor antagonist (e.g., spironolactone or eplerenone), or a pharmaceutically acceptable salt of one or both of the foregoing, and at least one matrix component, wherein the at least one matrix component is selected from the group consisting of: hydroxy propyl cellulose (HPC), hydroxypropyl methyl cellulose (HPMC), glyceryl behenate, and a polyethylene glycol glyceride. In an aspect, Torsemide and/or the aldosterone receptor antagonist (e.g., spironolactone or eplerenone), or the pharmaceutically acceptable salt of one or both of the foregoing, is present in the formulation in a range of about 1 wt % to about 20 wt %, or about 5 wt % to about 10 wt % and the matrix component is present in the formulation in a range of about 5 wt % to about 50 wt %, or about 15 wt % to about 35 wt %.

In an aspect, the extended-release oral dosage formulation may comprise about 5 wt % to about 10 wt % of Torsemide and/or an aldosterone receptor antagonist (e.g., spironolactone or eplerenone), or a pharmaceutically acceptable salt of one or both of the foregoing; about 10 wt % to about 40 wt % of a matrix component; about 50 wt % to about 60 wt % of at least one binder; about 5 wt % to about 15 wt % of lactose; about 1 wt % to about 3 wt % of talc; and about 0.5 wt % to about 1 wt % of magnesium stearate.

In another aspect, an extended-release oral dosage formulation may further comprise at least one binder, lactose, talc and magnesium stearate is provided, wherein the at least one binder present is a microcrystalline cellulose binder and is present in the formulation in a range of about 25 wt % to about 75 wt %, lactose is present in the formulation in a range of about 1 wt % to about 20 wt %, talc is present in the formulation in a range of about 1 wt % to about 5 wt %, and magnesium stearate is present in the formulation in a range of about 0.1 wt % to about 2 wt %.

In yet another aspect, the extended-release oral dosage formulation of Torsemide and/or an aldosterone receptor antagonist (e.g., spironolactone or eplerenone) may be combined with and/or comprise at least one of an ACE inhibitor, a calcium channel blocker, a thiazide diuretic, an angiotensin receptor blocker, an alpha blocker, potassium-sparing diuretic (e.g. Amiloride), central sympathetic suppressant (e.g. Moxonidine, Rilmenidine, Clonidine), and a beta-blocker, the ACE inhibitor is selected from the group consisting of: alacepril, benazepril, captopril, cilazapril, delapril, enalapril, enalaprilat, fosinopril, fosinoprilat, imidapril, lisinopril, perindopril, quinapril, ramipril saralasin acetate, temocapril, trandolapril, ceranapril, moexipril, quinaprilat and spirapril.

In yet another aspect, a method of making an extended-release oral dosage formulation comprising Toresemide and/or an aldosterone receptor antagonist (e.g., spironolactone or eplerenone) may comprise forming a mixture comprising at least a matrix component; wet granulating the mixture to form particles; sizing the particles; and forming the extended-release oral dosage formulation.

In a further aspect, a method of using the extended-release oral dosage formulation comprising Torsemide and/or an aldosterone receptor antagonist (e.g., spironolactone or eplerenone) may comprise administering a therapeutically effective amount of the formulation to a subject in need thereof. In a further aspect, a method of mitigating the reduction of an amount of GFR and/or increasing an amount of GFR may comprise administration of a therapeutically effective amount of the Torsemide ER formulations and/or an aldosterone receptor antagonist (e.g., spironolactone or eplerenone) described herein to a patient in need thereof. In a further aspect, a method of modulating fluid and/or Na$^+$ excretion may comprise administration of a therapeutically effective amount of the Torsemide ER formulations and/or an aldosterone receptor antagonist described herein to a patient in need thereof.

In yet a further aspect, administration of the extended-release oral dosage formulation comprising Torsemide and/or an aldosterone receptor antagonist leads to a novel mechanism for action in diuresis by acting on transporter in the kidney and/or acting on guanylate cyclase (GC), specifically membrane bound GC and modulated actions of peptide hormones such as brain natriuretic peptide (BNP) and atrial natriuretic peptide.

BRIEF DESCRIPTION OF THE FIGURES

FIG. 6A shows urine flow; FIG. 6B shows creatinine clearance; FIG. 6C shows sodium excretion; FIG. 6D shows potassium excretion. The mean values for the previous 24 hours are indicated by the horizontal dotted lines.

DETAILED DESCRIPTION OF THE INVENTION

Figure 1:
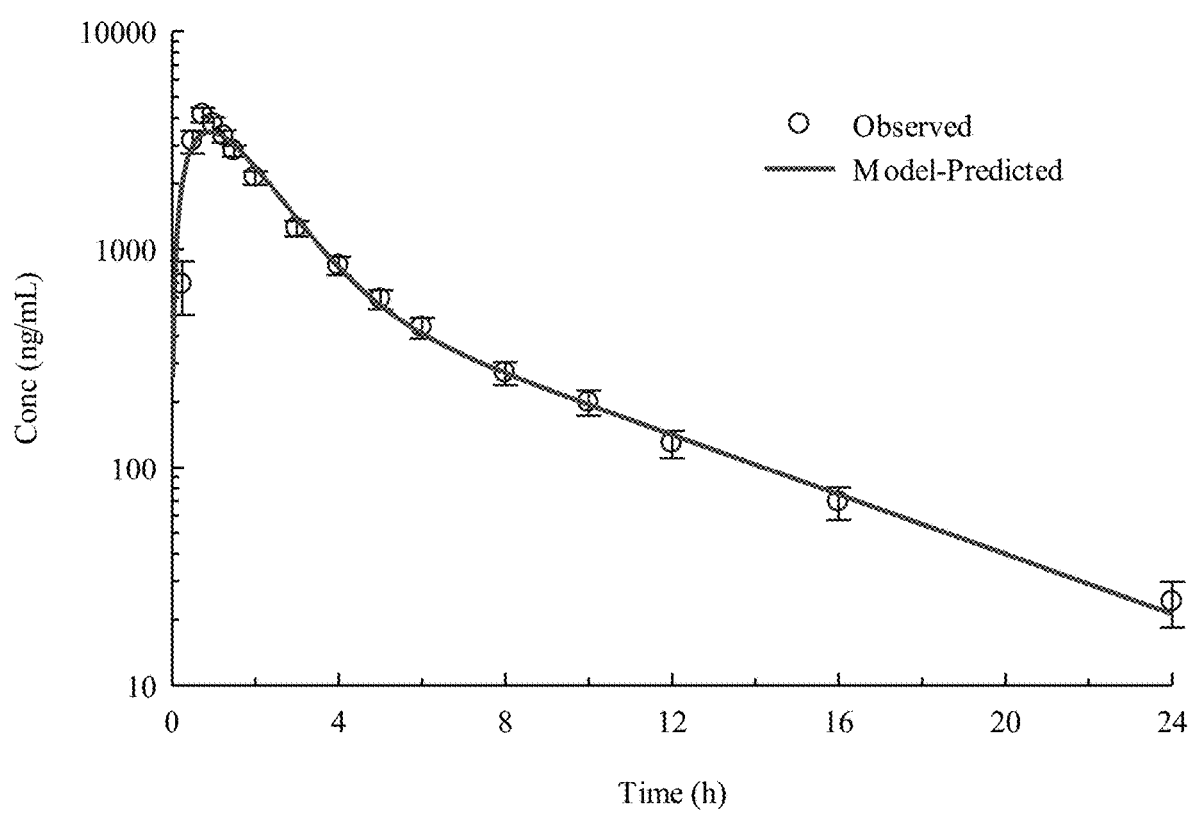
FIG. 1 shows observed (mean±standard error) and model-predicted Torsemide plasma concentrations after administration of a 20 mg IR formulation.

The present invention now will be described more fully hereinafter with reference to the accompanying figures, in which embodiments of the invention are shown. This invention may, however, be embodied in many alternate forms and should not be construed as limited to the embodiments set forth herein.

Modeling studies have shown that ER Torsemide may provide an improved diuretic therapy over IR Torsemide, particularly using a controlled-release loop diuretic. The molecular structure of Torsemide is shown below.

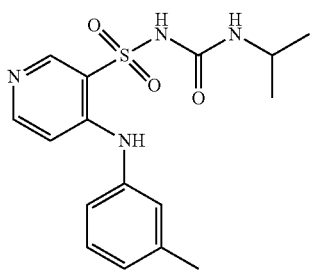 [SMILES: Cc1cccc(Nc2ccncc2S(=O)(=O)NC(=O)NC(C)C)c1]

ER formulations comprising Torsemide may comprise, as a controlled-release agent, a matrix based on erosion-controlled polymers and/or a matrix based on lipids and fatty acids.

Erosion Controlled Polymer Based Matrix Tablet Formulations

Matrix technologies based on hydrophilic polymers have proven popular among the oral controlled drug delivery technologies because of their simplicity, ease in manufacturing, high level of reproducibility, stability of raw materials and dosage forms, ease of scale-up and process validation. Due to these advantages, the matrix tablet platform may be used for Torsemide ER formulations.

Polymers with varying chemistry/molecular weights, for example Hydroxy Propyl Cellulose (HPC), Hydroxypropyl methyl cellulose (HPMC) may be used so as to target the drug release from the matrix independent of pH. Torsemide may be mixed with polymers and other excipients, this mixture may then be wet granulated, dried and sized, then compressed into tablet form. The polymer may be added into the formulation in the concentration between about 5% and about 50% based on the total tablet weight, preferably between about 10% and about 40%, and more preferably between about 15% and about 35% based on the total tablet weight. If required, pore formers may be added into the formulation to facilitate drug diffusion from the matrix. Since the solubility of Torsemide is low in water, medium and low molecular weight polymers may be used for granulation.

Lipid and Fatty Acid Based Tablet Formulations

Lipid excipients may be utilized to deliver clinically relevant sustained drug release profiles (8, 12, 24 hours) through the creation of an insoluble matrix structure from which diffusion is the principal drug extended-release mechanism.

Many lipid and fatty acid based excipients may be used as a release controlling agent. A few of the excipients such as glyceryl behenate (e.g. Compritol) and polyethylene glycol glyceride (e.g. Gelucire) may be used for the development of ER tablets. These lipid excipients produce ER release tablet matrices with pH independent release kinetics. These tablets may be made using simple techniques that yield highly stable drug release profiles. Drug release profile may be modulated by the addition of hydrophilic diluents like lactose or water-insoluble diluents depending on the desired kinetics and tablet characteristics. A target profile as described in Table 1 (below) may be used as reference.

TABLE 1

Target Profile Release Percentage.

| Time in Hr | Target Profile Torsemide Release in % |
|---|---|
| 1 Hr | 15-21 |
| 4 Hr | 50-65 |
| 8 Hr | 65-75 |
| 12 Hr | 80-95 |

The oral dosage ER Torsemide formulation may comprise Torsemide in a range of about 1 wt % to about 20 wt %. More preferably, the Torsemide may be present in a range of about 5 wt % to about 10 wt %. Most preferably, the Torsemide may be present in a range of about 6 wt % to about 7 wt %. Alternatively, the oral dosage ER Torsemide formulation may comprise Torsemide in a range of about 5 mg to about 50 mg. More preferably, the Torsemide may be present in a range of about 10 mg to about 40 mg or about 20 mg to about 30 mg. Most preferably, the formulation comprises 20 mg of Torsemide.

The matrix component (e.g., erosion-controlled polymer and/or lipid/fatty acid) may be comprised in the oral dosage formulation in a range of about 1 wt % to about 50 wt %. More preferably, the matrix component may be present in a range of about 10 wt % to about 40 wt %. Most preferably, the matrix component may be present in a range of about 15 wt % to about 35 wt %. Alternatively, the oral dosage ER Torsemide formulation may comprise the matrix component in a range of about 10 mg to about 90 mg. More preferably, the matrix component may be present in a range of about 20 mg to about 70 mg or about 30 mg to about 50 mg.

The ER oral dosage formulations may also comprise other ingredients, such as a binder or binders, lactose, talc and magnesium stearate.

The binder may be comprised in the oral dosage formulation as a single binder or a plurality of binders, for example a primary binder (e.g., by wt %) and a secondary binder, or binders. The primary binder may be a cellulose binder, and is preferably a microcrystalline cellulose binder such as Avicel PH 302, Avicel PH 101 and/or Avicel PH 102. The primary binder may be present in the oral dosage ER formulation in a range of about 25 wt % to about 75 wt %. More preferably, the primary binder may be present in a range of about 50 wt % to about 60 wt %. Most preferably, the primary binder may be present in a range of about 50 wt % to about 57 wt %. Alternatively, the oral dosage ER Torsemide formulation may comprise the primary binder in a range of about 50 mg to about 200 mg. More preferably, the primary binder may be present in a range of about 60 mg to about 150 mg or about 80 mg to about 100 mg.

Secondary binders, such as a polyvinylpyrrolidone (e.g., PVP K 30), may also be included in smaller wt % ranges, such as about 1 wt % to about 10 wt %, or more preferably 3 wt % to about 9 wt %. Alternatively, the oral dosage ER Torsemide formulation may comprise the secondary binder in a range of about 1 mg to about 20 mg. More preferably, the secondary binder may be present in a range of about 5 mg to about 15 mg.

Lactose may be present in the oral dosage ER formulation in a range of about 1 wt % to about 20 wt %. More preferably, lactose may be present in a range of about 5 wt % to about 15 wt %. Most preferably, lactose may be present in a range of about 8 wt % to about 14 wt %. Alternatively, the oral dosage ER Torsemide formulation may comprise lactose in a range of about 5 mg to about 50 mg. More preferably, lactose may be present in a range of about 10 mg to about 25 mg.

Talc and magnesium stearate may be present in the oral dosage ER formulation. Talc may be present in a range of about 1 wt % to about 5 wt %. More preferably, talc may be present in a range of about 1 wt % to about 3 wt %. Alternatively, the oral dosage ER Torsemide formulation may comprise talc in a range of about 1 mg to about 10 mg. More preferably, talc may be present in a range of about 2 mg to about 5 mg.

Magnesium stearate may be present in a range of about 0.1 wt % to about 2 wt %. More preferably, magnesium stearate may be present in a range of about 0.5 wt % to about 1 wt %. Alternatively, the oral dosage ER Torsemide formulation may comprise magnesium stearate in a range of about 0.5 mg to about 5 mg. More preferably, magnesium stearate may be present in a range of about 1 mg to about 2 mg.

The ER oral dosage Torsemide formulation may be used alone or in combination with other therapeutic agents such as, without limitation, ACE inhibitors, calcium channel blockers such as amlodipine, thiazide diuretics, angiotensin receptor blockers (ARBs) and alpha and beta-blockers. The other therapeutic agents may be administered with the ER Torsemide either sequentially or simultaneously. If administered simultaneously, a single capsule having a fixed ratio of the active agents may be used. If administered sequentially, the active agents may be used in multiple, separate capsules.

A combination therapy may comprise three active agents, such as an ACE inhibitor, an aldosterone receptor antagonist and a loop diuretic. For the ACE inhibitor and a loop diuretic combination, the formulations may comprise a weight ratio range from about 0.5% to about 1% based on the total tablet weight. These same agents may be present in the formulations in ratios of about 20:1 of the ACE inhibitor to the loop diuretic.

Examples of ACE inhibitor, which may be used in the combination therapy, may be selected from the group consisting of: alacepril, benazepril, captopril, delapril, enalapril, enalaprilat, fosinopril, fosinoprilat, imidapril, lisinopril, perindopril, quinapril, ramipril saralasin acetate, temocapril, trandolapril, ceranapril, moexipril, quinaprilat and spirapril.

Methods of making the ER oral dosage Torsemide formulations described herein are not particularly limited and may comprise: forming a mixture comprising Torsemide, a matrix component and other ingredients, granulating (e.g., wet granulating) the mixture to form particles, drying the particles, sizing the particles and forming an oral dosage controlled-release formulation, such as a tablet.

Methods of using the ER oral dosage Torsemide formulations described herein to treat the aforementioned conditions and diseases are also not particularly limited and may comprise administering a therapeutically effective amount of Torsemide to a subject in need thereof.

In-Vitro Studies

Example 1

In-vitro studies using Torsemide ER formulations were carried out and several ER formulations were used, including those based on an erosion-controlled, polymer-based matrix and a lipid/fatty acid based matrix.

For erosion-controlled, polymer-based matrix tablet formulations, Hydroxy Propyl Cellulose (HPC) was used as a controlled-release agent. Details of the release profile obtained from in-vitro stability studies are shown in Table 2 below.

TABLE 2

Release Profiles for ER Torsemide using HPC.

| S.No. | Ingredients (mg) | B.No. 11-173-01 | B.No. 11-173-03 | B.No. 11-173-04 | B.No. 11-173-05 | B.No. 11-173-07 |
|---|---|---|---|---|---|---|
| 1 | Torsemide | 10 | 10 | 10 | 10 | 10 |
| 2 | Avicel PH 302 | 84 | 98 | 100 | 91 | 92 |
| 3 | HPC HXF PH | 51 | 50 | 47 | 50 | 45 |
| 4 | Lactose (Super Tab) | — | 14 | 15 | 21 | 25 |
| 5 | Talc | 4 | 2 | 2 | 2 | 2 |
| 6 | Mag-Stearate | 1 | 1 | 1 | 1 | 1 |
| | | 150 | 175 | 175 | 175 | 175 |

Details of in-vitro dissolution testing results are shown in Table 3 below.

TABLE 3

In-Vitro Dissolution Testing Results

| Time in Hr | Target Release Profile | B.No. 11-173-01 | B.No. 11-173-03 | B.No. 11-173-04 | B.No. 11-173-05 | B.No. 11-173-07 |
|---|---|---|---|---|---|---|
| 1 hr | 18 | 16.8 | 21.9 | 23.4 | 22.9 | 27.3 |
| 2 hr | 30 | 25.2 | 33.1 | 34.6 | 34.8 | 39.9 |
| 3 hr | 40 | 31.7 | 41.3 | 42.9 | 42.7 | 49.0 |
| 4 hr | 52 | 37.2 | 47.8 | 49.4 | 49.5 | 56.5 |
| 6 hr | 60 | 46.6 | 57.9 | 59.3 | 59.8 | 67.4 |
| 8 hr | 70 | 54.1 | 65.6 | 66.7 | 66.8 | 74.8 |
| 10 hr | 80 | 60.7 | 71.5 | 72.2 | 72.5 | 79.8 |
| 12 hr | 90 | 66.0 | 76.1 | 76.2 | 76.2 | 82.8 |

For lipid and fatty acid-based matrix tablet formulations, Compritol 888 was used as a lipid matrix. Details of the release profile obtained from in-vitro testing are shown in Table 4 below.

TABLE 4

Release Profiles for ER Torsemide using HPC.

| S.No. | Ingredients | B.No. 11-173-02 | B.No. 11-173-06 |
|---|---|---|---|
| 1 | Torsemide | 10 | 10 |
| 2 | Avicel PH 102 | 93 | — |
| 3 | Avicel PH 101 | — | 87 |
| 4 | Compritol 888 | 34 | 31 |
| 5 | Lactose Super Tab 30GR | 20 | 25 |
| 6 | PVP K 30 | 6 | 15 |
| 7 | Talc | 5 | 5 |
| 8 | Mag-Stearate | 2 | 2 |
| | Tablet Weight | 170 | 175 |

Details of in-vitro dissolution testing results are shown in Table 5 below.

TABLE 5

In-Vitro Dissolution Testing Results

| Time in Hr | Target Release Profile | B. No. 11-173-02 | B. No. 11-173-06 |
|---|---|---|---|
| 1 hr | 18 | 16.2 | 17.3 |
| 2 hr | 30 | 25.3 | 27.2 |
| 3 hr | 40 | 33.9 | 35.6 |
| 4 hr | 52 | 43.3 | 43.5 |
| 6 hr | 60 | 60.1 | 56.1 |
| 8 hr | 70 | 70.9 | 65.2 |
| 10 hr | 80 | 78.6 | 72.4 |
| 12 hr | 90 | 84.6 | 77.7 |

Figure 3:
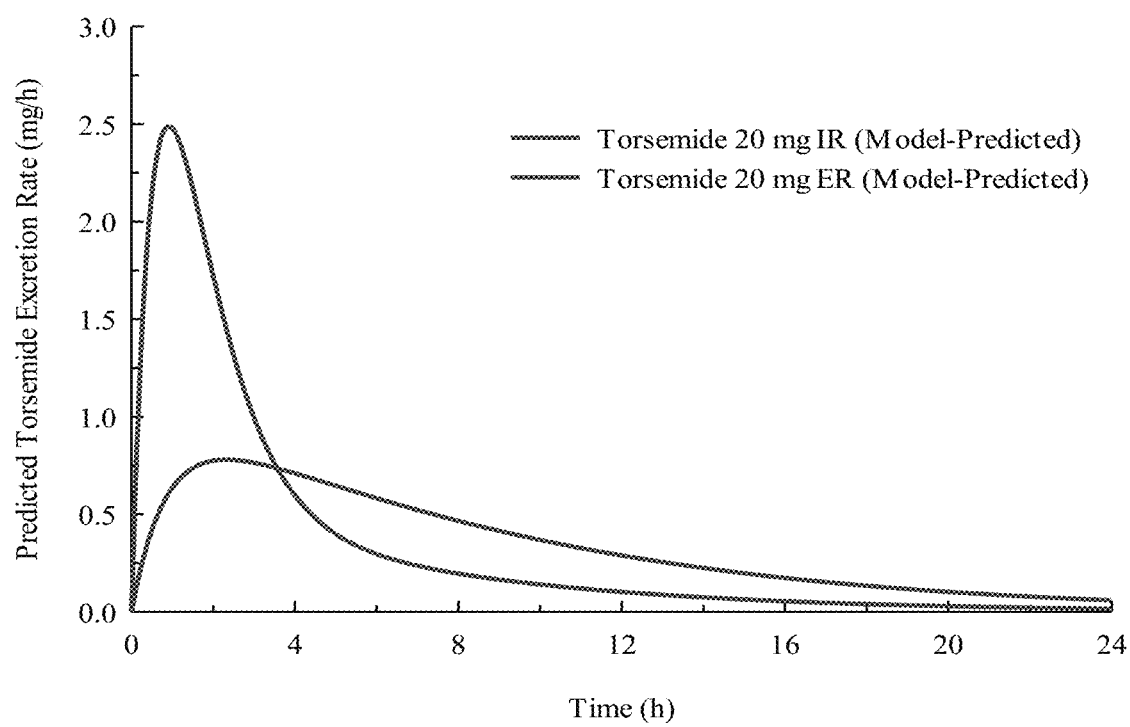
FIG. 3 shows model-predicted urinary Torsemide excretion rates after administration of 20 mg IR and ER formulations.
Figure 4:
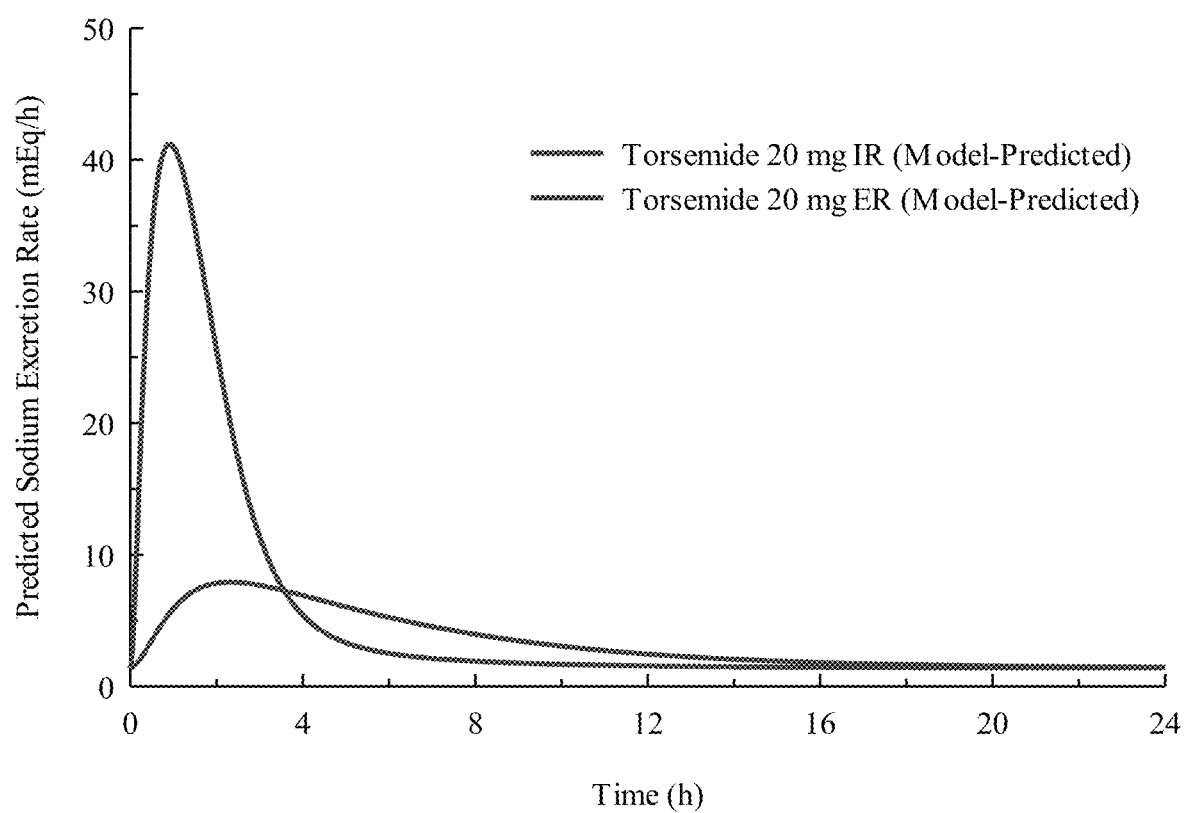
FIG. 4 shows model-predicted urinary sodium excretion rates after administration of 20 mg IR and ER formulations.
Figure 5:
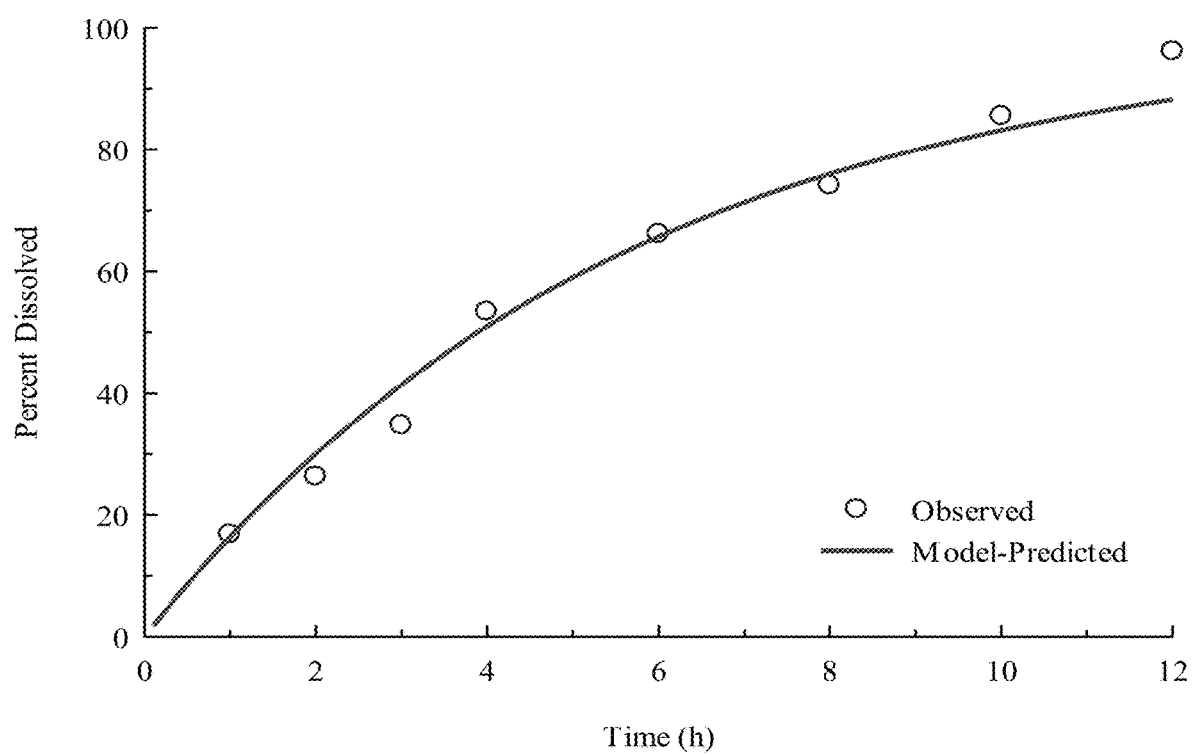
FIG. 5 shows observed and model-predicted percent dissolution of Torsemide from an ER oral dosage formulation.

Accordingly, the data listed in Tables 1-5 was used as a basis for the modeling curves shown in FIGS. 1-4 and part of FIG. 5.

FIG. 1 shows modeling of Torsemide plasma concentrations after administration of 20 mg IR and ER formulations. As can be seen, the ER formulation had a higher concentration of Torsemide 4 hours after administration than did the IR formulation.

Figure 2:
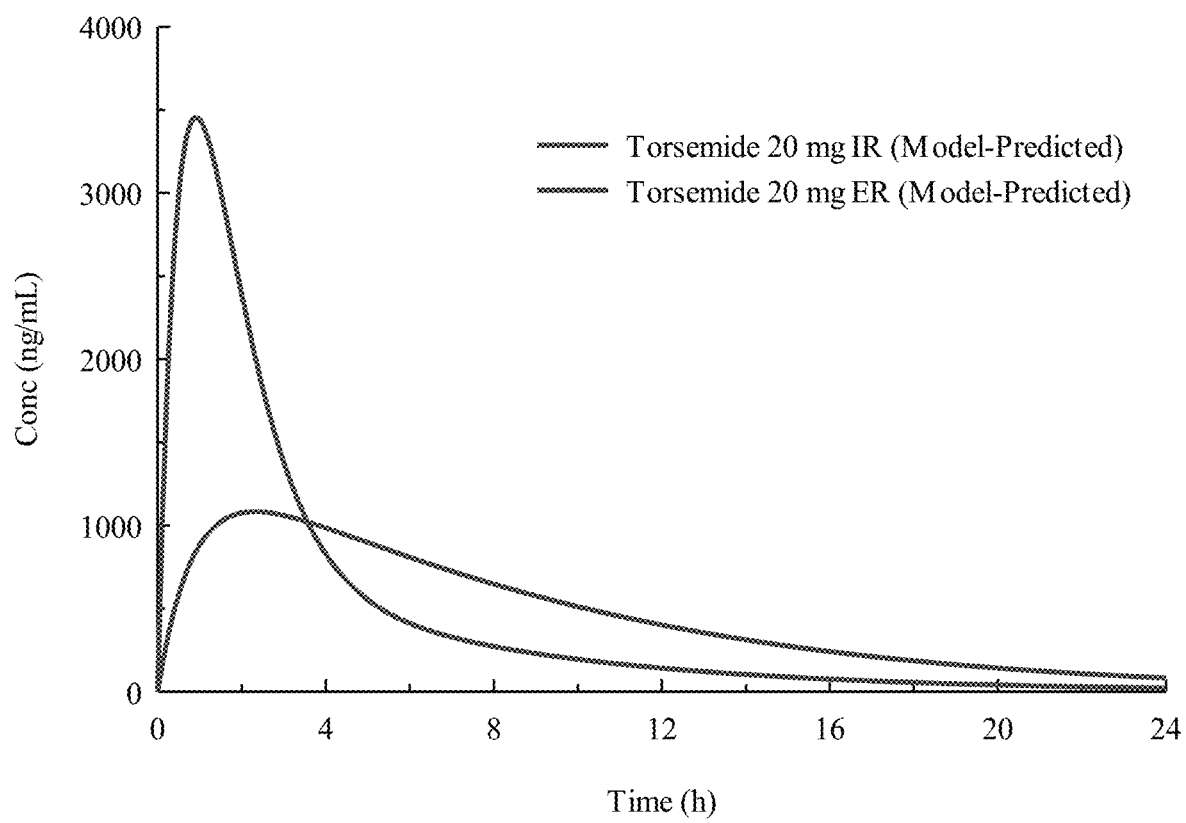
FIG. 2 shows model-predicted Torsemide plasma concentrations after administration of 20 mg IR and ER formulations.

FIG. 2 shows modeling of urinary Torsemide excretion rates of Torsemide after administration of 20 mg IR and ER formulations. As can be seen, much of the Torsemide of the IR formulation has been excreted within 4 hours of administration; whereas, much less of the Torsemide of the ER formulation was excreted in the same time period.

FIG. 3 shows modeling of urinary Torsemide excretion rates of Torsemide after administration of 20 mg IR and ER formulations. As can be seen, much of the Torsemide of the IR formulation has been excreted within 4 hours of administration; whereas, much less of the Torsemide of the ER formulation was excreted in the same time period.

FIG. 4 shows modeling of $Na^+$ excretion rates after administration of 20 mg IR and ER formulations. As can be seen, much of the $Na^+$ of the IR formulation has been excreted within 4 hours of administration; whereas, much less of the $Na^+$ of the ER formulation was excreted in the same time period.

FIG. 5 shows observed and model-predicted percent dissolution of Torsemide from an ER oral dosage formulation. As can be seen, the model-predicted data closely matches that of the experimentally observed data.

Example 2

Spironolactone has half-life of about 1.5 h. However, its metabolites such as canrenone has half-life of more than 15 hours. Spironolactone reaches steady state concentration in about 7-10 days. Side effects of spironolactone on serum potassium become most pronounced in about two-weeks. To optimize spironolactone release profile, we developed a formulation comprising HPMC, and other excipients. Example prototype formulations are given in Table 5.5 below:

TABLE 5.5

Example formulations using Spironolactone.

| S. No. | Ingredients | (mg) 16-12-01 | (mg) 16-12-02 | (mg) 16-12-03 |
|---|---|---|---|---|
| 1 | Spironolactone | 15 | 15 | 15 |
| 2 | MCC | 87 | 43 | 65 |
| 3 | HPMC | 43 | 87 | 65 |
| 4 | Silica | 24 | 28 | 26 |
| 5 | Lactose Super Tab 30GR | 10.5 | 17.5 | 14.5 |
| 6 | Talc | 5 | 5 | 5 |
| 7 | Mag-Stearate | 2.5 | 2.5 | 2.5 |
| | Total Tablet Weight | 187 | 198 | 193 |

Example 3

In-vivo studies comparing Torsemide IR (Demadex Rx) with an extended-release (ER) formulation prepared by Sarfez, Inc.

Subjects: Ten normal volunteers, aged 21 to 73 years were recruited. They had no significant past medical history, were not taking medications, and had normal values for blood urea nitrogen, serum creatinine, plasma electrolytes, liver function tests, hemogram, and urinalysis. All had a blood pressure less than 140/90 mmHg. Their body weights were 61.2 and 73.0 kg.

Trial Design: Each subject received both of the Torsemide preparations in a randomized crossover design separated by a 3-week washout period. Subjects were pre-consented, admitted, and received a fixed constant diet for 3 days containing 300 mmol per day sodium and 45 mmol per day of potassium. This was verified by ashing and analyzing the food items fed to the subjects. Throughout the 3 days, subjects remained in the metabolic ward. Each meal was observed to ensure that subjects ate all the food given to them. Subjects remained within the facility for the duration of the study. No visitors were allowed. This provided strict control of food, sodium, and potassium intakes. Fluid was allowed ad libitum. During day 2, subjects collected a 24-hour urine. Thereafter, there was a 2-hour period during which the subjects were prepared for the procedures on the experimental day. They were weighed, an intravenous cannula inserted, and blood pressure and heart rate taken using an automated device after 2 minutes of sitting. They were fasted for 12 hours prior to receiving the drug, and for 4 hours thereafter. To compensate for loss of salt intake (50 mmol of $Na^+$) during the breakfast period, they received 233 mL of 0.154 M saline solution immediately prior to drug administration. At zero time, they received 20 mg of Torsemide (IR or ER) with 300 mL of water. Immediately before ingestion, and for 23 hours thereafter, blood and urine samples were taken at designated times and another 24-hour urine was collected. After completion of the study, subjects were weighed, blood pressure and heart rate were recorded in the sitting position and they were discharged.

Analyses: Urine samples were measured for volume and aliquots taken. $Na^+$ and $K^+$ concentrations were measured in an automated apparatus with an ion selective electrode, and creatinine concentrations in a creatinine analyzer. Other aliquots were saved for measurement of Torsemide. A 35 ml blood sample was taken immediately prior to, and an 8 hour and 23 hours after the drug administration. This was analyzed for creatinine and for key hormones including plasma renin activity (PRA), serum aldosterone concentration (SAC), and brain natriuretic peptide (BNP).

Statistics: Mean±SEM data were calculated for each drug period in each individual subject. Within subject paired t-tests were used to assess differences in response to the IR versus DR preparations. A P value <0.05 were taken as statistically significant.

Figure 6:
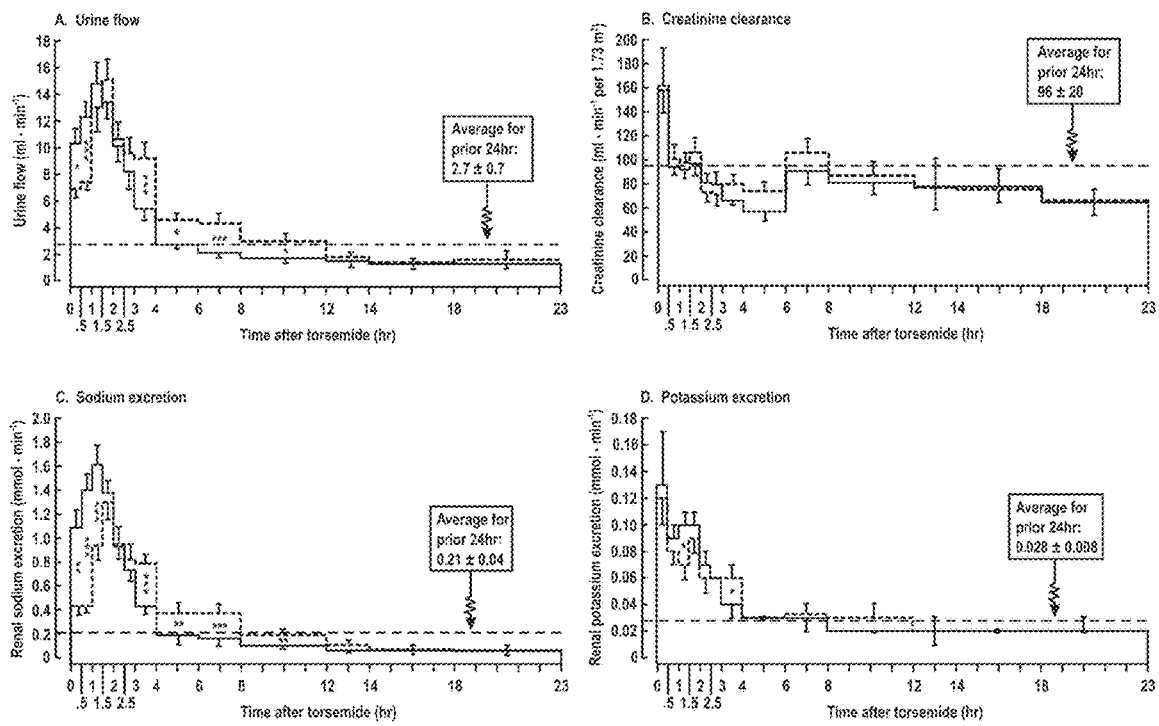
FIG. 6 shows Mean±SEM values (n=10 per group) for subjects receiving 20 mg of Torsemide as the IR preparation (continuous lines) or ER (dashed lines) as a function of time after Torsemide administration.

Results: All 10 subjects completed both arms of the trial without any adverse effects. The patterns of urine flow, creatinine clearance, sodium and potassium excretion following drug administration are shown in FIG. 6. The average values for the prior 24-hours are indicated by horizontal dotted lines. Urine flow increased rapidly with the IR preparation and was significantly greater than ER for the first hour (FIG. 6A). Both preparations achieved a similar maximal urine flow rate of circa 15 mL·min$^{-1}$. By 3 hours, urine flow was significantly greater with ER than IR and remained so until 12 hours.

There was an initial sharp increase in creatinine clearance during the first ½ hr after administration of both formulations of Torsemide (FIG. 6B), but this returned abruptly to baseline and was reduced below baseline at 2 hours where it remained during most of the period from 2-23 hours. There were no significant differences in creatinine clearance between IR and ER during these periods.

Sodium excretion increased rapidly with the IR preparation to a maximum of 1.6 mmol per minute by 1.0 to 1.5 hrs. (FIG. 6C). Thereafter, rates of Na$^+$ excretion with the IR and ER preparation were similar until 3 hours when Na$^+$ excretion was greater with ER. This difference remained until 12 hours.

Potassium excretion increased sharply with both preparations and remained elevated for about 4 hrs. (FIG. 6D). K$^+$ excretion was greater with IR from 1-1.5 hours and with ER from 3-4 hours, but generally followed a similar pattern. After 12 hours, K$^+$ excretion was low in both groups.

The individual values for excretion and creatinine clearance for the 24-hour period immediately before and for 24-hour immediately after drug administration demonstrates that fluid excretion was not significantly changed after IR, but was increased significantly after ER resulting in a significantly 2.2-fold greater fluid loss of 906 mL after ER versus IR (data not shown). The creatinine clearance was significantly reduced by 25% following IR, but was not significantly changed following ER (data not shown). Sodium excretion was increased significantly after both drugs, but the increased was significantly greater by 2.2-fold after ER (data not shown). Neither drug changed 24-hour potassium excretion.

Fluid excretion, Ccr, Na$^+$, K$^+$ excretion, FENa and FEK were not significantly different before administration of IR vs. ER (data not shown). A major difference between the responses to the two formulations is the greater loss of fluid and Na$^+$ after ER vs. IR. The GFR tended to fall after Torsemide (significant only for IR). The greater increased excretion of Na$^+$ after ER vs. IR was matched by a lesser reduction in GFR (and hence a better-preserved filtered load of Na$^+$). The outcome was that there was a similar increase in fractional excretion of sodium (FENa) after IR and ER. Both formulations tended to increase K$^+$ excretion (not significant for either). The outcome of a rather higher K$^+$ excretion with a rather lower GFR (and hence a reduced filtered load of K$^+$) was a consistent increase in fractional excretion of potassium (FEK) that was similar for both formulations (data not shown).

The body weight, blood pressure, heart rate and plasma data (data not shown) demonstrates that body weight decreased significantly only after ER. The diastolic blood pressure was increased after IR, but tended to fall after ER, resulting in a significantly greater reduction in diastolic and mean blood pressures after ER compared to IR. Heart rate was reduced after both formulations. There were similar increases in serum creatinine but no significant changes in serum sodium or potassium concentrations.

The pharmacokinetic data are shown in Table 6 below. Compared to IR, the $C_{max}$ with ER was reduced 69% and the AUC was reduced 18-21%. The $T_{max}$ was prolonged 2.5-fold with a 59% reduction in AUC from 1 to 3 hours but a 97% increase in AUC from 8-10 hours. The Kel was reduced 32% resulting in a 45% increase in $t_{1/2}$. The apparent $V_D$ was increased 79%. All of these differences were statistically significant.

TABLE 6

Pharmacokinetic Parameters after Administration of Torsemide: for Immediate Release and Delayed Release Formulations.

| Parameter | IR | DR | Fold difference | P value |
|---|---|---|---|---|
| $C_{max}$ (ng · ml$^{-1}$) | 2962 ± 412 | 905 ± 93 | −69 | <0.001 |
| $AUC_{0-t}$ (hr*/ng · ml$^{-1}$) | 6493 ± 688 | 5125 ± 552 | −21 | <0.001 |
| $AUC_{0-inf}$ (hr*/ng · ml$^{-1}$) | 6728 ± 704 | 5543 ± 565 | −18 | <0.001 |
| $T_{max}$ (hr) | 1.03 ± 0.13 | 3.53 ± 0.27 | +243 | <0.001 |
| $AUC_{1-3}$ (hr*/ng · ml$^{-1}$) | 2966 ± 294 | 1225 ± 161 | −59 | |
| $AUC_{8-10}$ (hr*/ng · ml$^{-1}$) | 203 ± 32 | 400 ± 50 | +97 | |
| Kel (hr) | 0.266 ± 0.03 | 0.194 ± 0.03 | −32 | |
| $t_{1/2}$ (hr) | 2.81 ± 0.25 | 4.07 ± 0.57 | +45 | |
| $V_D$ (ml) | 2498 ± 789 | 22414 ± 3139 | +79 | |

Mean ± Sem values
(n = 10 per group)

The main findings from this study are that a novel ER formulation of Torsemide that delivered the drug into solution over 12 hours led to a more prolonged period of natriuresis and diuresis and a two-fold larger loss of fluid and Na$^+$ than a traditional IR formulation. This resulted in a significant loss in body weight and a significantly greater reduction in diastolic and mean blood pressures. The $C_{cr}$ was reduced only after the IR preparation, which reduces the filtered load of Na$^+$. The combination of a greater loss of Na$^+$, but a better-preserved filtered load of Na$^+$ after the ER compared to the IR formulation resulted in similar increases in FENa. For both drugs, a period of diuresis, natriuresis and kaliuresis was followed by sustained renal fluid and electrolyte retention. Neither drug led to a significant loss of potassium but again the lower levels of GFR reduced the filtered load of K$^+$ and led to significant, and similar, increases in FEK with both formulations. The ER formulation prolonged the time to maximal plasma Torsemide concentration by 2.5 fold with a corresponding reduction in Torsemide plasma levels 1 to 3 hours after dosing, but a doubling of plasma levels 8-10 hours after dosing. The overall bioavailability was reduced by 18%. The combination of an enhanced Na$^+$ loss despite a reduced bioavailability implies that the ER formulation had increased the diuretic efficiency.

The daily intake of Na$^+$ in this study of 300 mmol was designed to match prior studies in normal subjects given furosemide. The IR formulation of Torsemide (20 mg) did not increase fluid excretion or weight loss over 24 hours but led to a modest, but significant, Na$^+$ loss of 42 mmol.

Torsemide ER led to a similar maximal naturiuresis as IR, but the peak was delayed by about 1 hour. The main effect of the ER preparation was to prolong the period of Na$^+$ and fluid loss (relative to the IR) by four-fold. This led to a significantly greater fluid and Na$^+$ loss with the ER formulation. These greater salt and water depleting actions of Torsemide ER were accompanied by significant reductions in body weight only after ER and by significantly greater reductions in diastolic and mean blood pressure after ER.

Therefore, the present findings that an ER formulation of Torsemide led to significantly more Na+ and fluid loss than an IR preparation and that only the ER preparation increased fluid excretion and reduced body weight and diastolic blood pressure, carries clinical impact since these studies were conducted at a high level of salt intake. They raise the possibility that dietary salt restriction may not be absolutely required to achieve predictable salt and water loss and a reduction in blood pressure during treatment of patients with hypertension or CHF with ER Torsemide.

This study supports the hypothesis that a more prolonged duration of loop diuretic action enhances fluid and Na+ loss. This study also confirms the hypothesis that a more prolonged duration of action of a loop diuretic would prolong the sojourn of plasma levels in the most efficient 25-70% of maximal range and in an improvement in overall natriuretic efficiency.

The regulation of GFR by loop diuretics is complicated and unresolved. Two factors have been identified that may increase the measured GFR. There is an artifactual initial increase caused by flushing out of concentrated GFR markers from the tubules by the abrupt increase in urine flow, as seen in the first 30 minutes of this study (FIG. 6B). Second, inhibition of tubuloglomerular feedback would reduce afferent arteriolar resistance and should increase the GFR. Three factors have been identified that may reduce the GFR. Inhibition of fluid reabsorption raises the intertubular pressure substantially, which will limit the force for glomerular filtration. Second, the release of vasoactive agents could reduce the renal blood flow. Third, depletion of body fluid can cause renal vasoconstriction. The present study demonstrated that, after the early (artifactual) increase in GFR, there was a rapid return to baseline and below resulting in a significant 25% reduction in creatinine clearance in the 24 hours after Torsemide IR. This constitutes a serious adverse effect since even modest reductions in GFR, especially when accompanied by release of vasoactive hormones, increases the risk of CVD and limit antihypertensive and fluid-depleting efficacy.

Thus, these results demonstrate that an ER formulation of Torsemide increased fluid and Na+ loss and mitigated significant reductions in GFR, compared to the IR formulation. Thus, a method of mitigating the reduction in GFR and/or the increase in GFR may comprise administration of a therapeutically effective amount of the Torsemide ER formulations described herein to a patient in need thereof. Also, a method of increasing fluid and/or Na+ loss may comprise administration of a therapeutically effective amount of the Torsemide ER formulations described herein to a patient in need thereof.

It has also been surprisingly found that the Torsemide ER formulations described herein, when administered, lead to a novel mechanism for Torsemide action in diuresis. It is known that torsemide acts on Na+/K+/2Cl− co-transporter in the kidney. It has been found that Torsemide also interacts with guanylate cyclase (GC), specifically membrane bound GC (mGC) and modulated actions of peptide hormones such as brain natriuretic peptide (BNP) and atrial natriuretic peptide. Structurally, torsemide is similar to atrial natriuretic peptide (ANP) and can compete for binding to its receptor. However, other members of the loop diuretic class such as furosemide cannot compete with ANP for binding to its receptor due to structural differences. Torsemide mediated modulation of GC, specifically mGC induces changes in cGMP and cGMP mediated pathways.

In an embodiment of the present invention, an extended release oral dosage formulation is considered wherein a tablet is manufactured by wet granulation comprising torsemide or a pharmaceutically acceptable salt thereof as an active ingredient ranging from 27%-34% by weight hydroxypropyl methyl cellulose and 25-53% by weight high-density microcrystalline cellulose of nominal particle size of about 100 micrometers; and 6.5-8% lactose monohydrate. In a preferred embodiment, when administered orally to a subject the $T_{1/2}$ will increase between 32-55% compared to that of a corresponding (by API weight) immediate release dosage form. In another embodiment, an aldosterone receptor antagonist or a pharmaceutically acceptable salt thereof is added, wherein torsemide and the aldosterone receptor antagonist are part of the extended release dosage formulation.

In another embodiment of the present invention, an extended release oral dosage formulation is considered wherein a tablet is manufactured by wet granulation comprising torsemide or a pharmaceutically acceptable salt thereof as an active ingredient ranging from 27%-34% by weight hydroxypropyl methyl cellulose and 25-53% by weight high-density microcrystalline cellulose of nominal particle size of about 100 micrometers; and 5-8% lactose monohydrate.

In another embodiment, the extended release oral dosage formulation will be administered orally to a subject, and $C_{max}$ decreases by 60-76% of a corresponding (by API weight) immediate release dosage form. In a preferred embodiment, the extended release oral dosage formulation when administered orally to a subject shall decrease AUC1-3 (1-3 hours after drug administration and measured as hr/ng·ml-1) between 48-67% and increases AUC8-10 (8-10 hours after drug administration and measured as hr/ng·ml-1) between 149-263% compared to that of a corresponding (by API weight) of the immediate release dosage form.

In another embodiment, a method of producing wet granules of an extended release oral dosage formulation is contemplated wherein mixing torsemide with either 27-34% by weight or 32-34% by weight hydroxypropyl methyl cellulose with 25-53% by weight of high-density microcrystalline cellulose, and 5-8% by weight of lactose monohydrate results in a final weight of granules.

It is an object of the present invention to provide an extended release oral dosage formulation with torsemide and a matrix component. Further, the matrix component may be selected from HPC, HPMC, glyceryl behenate, or a polyethylene glycol glyceride and combinations thereof. The formulation can be formed into a tablet for dosing. The concentration of torsemide may vary from a range of about 0-20% by weight. In alternative embodiments, the Torsemide may be present in ranges of 5-10% by weight or up to 50% by weight. A binder may be used in the extended oral release dosage form and be between 25-75% of the formulation by weight. In certain embodiments, the binder may be a microcrystalline cellulose binder.

In alternative embodiments, lactose or lactose monohydrate may be used in a range of 0-20% by weight. For treatment in patients with diabetes, an extended oral release formulation is contemplated and torsemide is present in conjunction with an ACE inhibitor, an aldosterone receptor antagonist, a calcium channel blocker, a thiazide diuretic, an angiotensin receptor blocker, an alpha blocker, and a beta blocker.

The ACE inhibitor aspect can be alacepril, benazepril, captopril, cilazapril, delapril, enalapril, enalaprilat, fosinopril, fosinoprilat, imidapril, lisinopril, perindopril, quinapril, ramipril saralasin acetate, temocapril, trandolapril, ceranapril, moexipril, quinaprilat and spirapril.

The method of making the formulation contains the steps of forming a mixture of torsemide and a matrix component, granulating the mixture into particles and sizing them, and re-forming the mixture into an extended release tablet formulation. Preferred embodiments include about 5 wt % to about 10 wt % of Torsemide or a pharmaceutically acceptable salt thereof; about 10 wt % to about 40 wt % of a matrix component; about 50 wt % to about 60 wt % of at least one binder; about 5 wt % to about 15 wt % of lactose; about 1 wt % to about 3 wt % of talc; and about 0.5 wt % to about 1 wt % of magnesium stearate.

Alternative tablet formulations provide for about 6-7% by weight of torsemide and 15-35% by weight of the matrix component. The matrix component can be hydroxy propyl cellulose (HPC), hydroxypropyl methyl cellulose (HPMC), glyceryl behenate, a polyethylene glycol glyceride and combinations thereof.

In an embodiment, the present invention comprises a combination therapy of a Sodium-glucose linked transporter (SGLT) inhibitors and torsemide in an extended release formulation for prevention and treatment of recurrent heart failure (HF) in patients with type 2 diabetes (T2D) and chronic kidney disease (CKD).

SGLT inhibitors are currently marketed as adjunctive therapy for type 2 diabetes mellitus (T2D). They include empaglifozin, canaglifozin, dapaglifozin and ertugliflozin. In clinical trials, SGLT inhibitors have shown substantial reduction in cardiovascular (CV) events; hospitalization for HF, and mortality. Although the glycosuric effect of SGLT inhibitors is diminished progressively in chronic kidney disease (CKD) and they have little effect on reducing HbA1c at eGFR >50 ml/min. However, they have shown to improve CV outcomes and reduced mortality in patients with eGFR <50 ml/min despite reduced effect on HbA1c. The improved CV outcomes are accompanied by weight loss and fall in blood pressure (BP). These effects were confirmed for empagliflozin and dapagliflozin. These data suggest that although CKD limits the efficacy of SGLT inhibitors in reducing HbA1c, since CKD limits the load of glucose filtered by the kidney and hence the renal excretion of glucose, the diuretic and natriuretic effects are still preserved. However, these studies were limited to patients with eGFR >30 ml/min whose mean eGFR was 54 ml/min (CKD3a). The effect of SGLT inhibitors on CVD and GFR protection are expected to the same specifically in patients with CKD 3b or 4.

Mechanism of diuretic and natriuretic efficacy of SGLT inhibitors in CKD: It was originally assumed that increased urine output and sodium excretion in patients with T2D treated with SGLT inhibitors represented an osmotic diuresis from the effects of the large increase in excretion of glucose. However, this cannot explain their maintained, or ever improved diuretic, natriuretic and antihypertensive effectiveness in CKD where glycosuria is minimal. This has been modeled recently based on renal micropuncture data in a T2D rat with CKD induced by 5/6 nephretomy (nx). The model predicts that in a 5/6 Nx T2D rat, there would be higher luminal glucose delivery (due to hyperfiltration in remaining nephrons) that will enhance the effect of SGLT inhibitors to increase tubular fluid glucose concentration. Since the proximal tubule (PT) is highly permeable, this will reduce PT fluid reabsorption and consequently reduce the tubular fluid [Na] to such an extent that net paracellular Na+ transport in the permeable S3 segment of the proximal tubule downstream from the site of action of SGLT inhibitors (S2 segment) is reversed, leading to substantial net tubular Na+ secretion into the tubular fluid. Thus, SGLT inhibitors provide unexpectedly good adjunctive diuretic therapy for HF in T2D in patients with CKD 3b/4, but they are not sufficient as solo therapy for HF. Moreover, combined SGLT1 and 2 inhibitors therapy could enhance this effect by further reducing glucose reabsorption and tubular fluid [Na] in the proximal tubule that should further enhance tubular Na+ secretion.

Mechanism of preservation of GFR by SGLT inhibitors in diabetic nephropathy: Most patients with T2D have "hyperfiltration" due to reduced pre-glomerular (afferent arteriolar) tone that increases the glomerular capillary pressure ($P_{GC}$) and glomerular plasma flow and thereby increases the single nephron glomerular filtration rate (SNGFR). Reduced afferent arteriolar tone in T2D is attributed to inhibition of voltage gated calcium channels by hyperglycemia. The mechanism of renal protection in patients with diabetic nephropathy by renin system inhibitors entails a differential reduction in the post-glomerular (efferent arteriolar) tone that reduces the $P_{GC}$. SGLT inhibitors have been shown to correct hyperfiltration by a unique mechanism distinct from ACEI's or ARB's. Thus, inhibition of Na+/Cl– and glucose reabsorption in the PT increase the delivery of Na+ and Cl– to the loop of Henle and the macula densa segment. The increased Na+/Cl– delivery activates the tubulo-glomerular feedback (TGF) response to cause vasoconstriction of the afferent arteriole that corrects the hyperfiltration. This activation of TGF is maintained over 2 weeks of observation of SGLT inhibitor administration to diabetic rats. Activation of TGF should produce an initial fall in GFR and renal blood flow (i.e., correction of hyperfiltration), followed by a stabilization over time, as was indeed seen in patients with diabetic nephropathy. For example, empagliflozin caused an acute fall in GFR and renal blood flow (RBF) in patients with T1D. Thus, SGLT inhibition provides an exciting and novel approach to prevent loss of GFR in diabetic nephropathy that should be additive with the effects of ACEIs and ARBs but effects in patients with more than modest CKD are not presently explored. This is a group in greatest need since most physicians withdraw ACEIs and ARBs in patients with CKD3b and beyond. Moreover, hyperkalemia in this group can present an urgent need to change therapy. SGLT inhibitor and loop diuretics both have $K^+$ losing, rather than $K^+$ retaining, actions that would be beneficial in these patients and thereby would fill an unmet need. Indeed, an additive hypokalemic effect of an SGLT inhibitor and a loop diuretic over one week are shown in healthy subjects. A combination of SGLT inhibitor/loop diuretic provides a unique opportunity to combat or prevent hyperkalemia and thereby to liberalize much needed ACE/ARB/MCA therapy. In addition, any preservation of eGFR by SGLT inhibitor therapy should improve CV and HF outcomes since a reduction in GFR is a strong predictor of adverse outcomes in CHF. However, acute inhibition of SGLT1/2 with phlorizin reduces RBF and GFR in diabetic rat (i.e., corrected hyperfiltration) similar to effects of a SGLT inhibitor alone.

Synergy between SGLT inhibitors with loop diuretic: Repeated administration of an SGLT inhibitor to rats with T2D led to a sustained reduction in the fraction of filtered $Na^+$ and $Cl^-$ reabsorbed in the proximal tubule and yet enhanced the fraction of $Na^+$ and $Cl^-$ reabsorbed in the loop of Henle. If the loop of Henle is reabsorbing more $Na^+$ and $Cl^-$ during SGLT inhibitor therapy, loop diuretics that inhibit coupled $Na^+/K^+/2Cl^-$ reabsorption in the loop of Henle should become more effective. This hypothesis was tested in a cross-over trial of healthy volunteers where dapagliflozin alone produced only a modest natriuresis. A loop diuretic, bumetanide, produced a bigger natriuresis. However, when given after one week of dapaglifozin therapy, the natriuresis with bumetanide was 36% greater. Moreover, when given after one week of bumetanide therapy, the natriuresis with dapagliflozin was 190% greater. These data demonstrate two-way adaptive natriuretic synergy between a SGLT inhibitor and a loop diuretic. Thus, a SGLT inhibitor and loop diuretic is an ideal combination for patients with CHF with T2D.

Torsemide ER an improved loop diuretic: Furosemide is the most widely prescribed loop diuretic but it suffers from several defects: highly variable bioavailability (10-80%), frequent hypokalemia and inability to reduce BP in essential hypertension. In contrast, torsemide has high and predictable bioavailability of 80-100% that is unaffected by CHF or CKD, it does not cause hypokalemia at usual therapeutics doses and is a good anti-hypertensive agent. This has led to the suggestion that torsemide be the loop diuretic of choice for CHF. Indeed, in a head-to-head comparison of patients with HF randomized to furosemide or torsemide on discharge from hospital with acute HF, those receiving torsemide had approximately half the number of readmissions for HF over the follow up period. Despite high bioavailability and low variability of torsemide compared to furosemide, it too, like all other loop diuretics, suffers from a very short (3-5 hour) duration of action, which leaves the nephron available to reabsorb Na+ and fluid during the time after the diuretic has been eliminated and the thereby limits their therapeutic efficacy. Moreover, the torrential diuresis ("Niagara effect") is distressing for elderly patients and can cause incontinence that contributes to non-compliance. Accordingly, extended release torsemide was developed that has 8-12-hour duration of action in vivo studies. In a crossover trial with normal volunteers, torsemide ER led to twice the loss of Na+ and fluid in 24 h after a single dose, accompanied by a fall in body weight, but no increase in K+ excretion; whereas, the subjects receiving torsemide immediate release, similar to those in prior trials with furosemide, had a significant 22% reduction in GFR, when given torsemide ER, there was no significant fall in GFR. Almost all patients with CHF and CKD 3 or 4 require a loop diuretic, and failure of loop diuretic efficacy is a major cause for relapse and readmission from CHF. Thus, a combination of a SGLT inhibitor with torsemide ER provides the best available Na+ and fluid-depleting therapy and to provide superior clinical outcomes in patients with T2D, CKD and/or CHF.

SGLT1 vs. SGLT2 inhibitors: SGLT1 is co-expressed with GLUT1 in the GI Track (GIT), heart and S3 segment of the proximal tubule. Sotagliflozin is an SGLT1/2 inhibitor that can improve glycemic control and may address unmet needs. The SGLT1 inhibition component impairs glucose absorption in the GIT and thereby moderates post-prandial hyperglycemia. Assuming the GIT effects are preserved in CKD, this may provide additional HbA1c lowering effect due to SGLT1 inhibition. Recent studies in patient with T1D and CKD3b indicates that SGLT1/2 inhibitors are better in reducing HbA1c in these patients as compared to SGLT2 specific inhibitors. Clearly, these studies need to be confirmed in a large group of patients but SGLT1/2 inhibitors hold promise.

Anti-cardiac fibrotic effects of a SGLT inhibitor and torsemide ER combination: The beneficial effects of SGLT inhibition on HF are apparent within a few weeks, and generally are not achieved with other anti-hyperglycemic drugs. This has led to the suggestion that they may have direct cardiac effects. One potential mechanism shown for dapagliflozin in a rat model of myocardial infarction is an anti-oxidant/anti-fibrotic action. The mechanism is clear and entails reduced collagen-1 cardiac accumulation. Nonetheless, SGLT2 is not expressed in the human heart, and the benefits of dapagliflozin may have been mediated in part via off-target effects on SGLT1. Similarly, animals or patients with CHF treated with torsemide also have reduced cardiac fibrosis. This effect is specific for torsemide and is not seen with furosemide. The mechanism seems to be independent of mineralocorticoid receptor (MCR) inhibition or aldosterone receptor antagonist. Torsemide also prevents cardiac fibrosis in a rat model of CKD. Thus, both SGLT2 inhibitors and torsemide can inhibit cardiac fibrosis in models or patients with CHF and CKD perhaps by independent and additive mechanisms.

Compared to present therapy with a SGLT inhibitor and furosemide for patients with T2D, CHF and CKD, a novel combination of a SGLT inhibitor with torsemide ER is expected to have the following benefits:
1. Enhanced Na+ and fluid loss providing enhanced protection from recurrent CHF,
2. Enhanced reduction in HbA1c providing anti-hyperglycemic efficacy at more advanced levels of CKD,
3. Enhanced Quality of Life (QoL) with less Niagara effect and incontinence leading to better compliance,
4. Enhanced protection against hyperkalemia thereby opening a window of opportunity to liberalize ACEI/ARB/MCR antagonist therapy,
5. Enhanced anti-fibrotic effects in the heart and vasculature that may be especially beneficial in patients with HF and preserved ejection fraction, preventing development of HF in patients with diabetes, CKD and/or HT, who currently lack a targeted therapy.

TABLE 7

Dosage Formulations and Selectivity for SGLT2 and SGLT1

| Chemical Entity | Bioavailability | $T_{max}$ (h) | $T_{1/2}$ (h) | Dose (mg) | Selectivity (SGLT2:SGLT1) |
|---|---|---|---|---|---|
| Canagliflozin | 65% | 1-2 | 10 | 100-300 | 1:414 |
| Dapagliflozin | 78% | 1-1.5 | 13 | 5-10 | 1:1200 |
| Empagliflozin | 95% | 1.5 | 13 | 10-25 | 1:2500 |
| Ertugliflozin | 87% | 2-3 | 12.5 | 5-15 | 1:2000 |
| Ipragliflozin | 92 | 1 | 15 | | 1:360 |
| Tofogliflozin | 98% | 1.1 | 5.5 | | 1:3000 |
| Sotagliflozin | 70% | 1.9 | 2.5 | | 1:20 |

Uncontrolled or resistant hypertension is common. It is defined as a blood pressure that is not at goal despite the prescription of a diuretic and two other antihypertensive drugs. It carries an increased risk of cardiovascular and cerebrovascular complications because of the adverse effects of sustained hypertension. It frequently complicates hypertension in patients with chronic kidney disease (CKD) or diabetes mellitus (DM) in whom hyperkalemia is a recognized complication of therapy with drugs that block the renin-angiotensin-aldosterone system (RAAS). The recently published PATHWAY-2 trial reported that spironolactone was very effective in reducing BP in this population and related this to a high proportion of such patients with hyperaldosteronism. Despite their effectiveness, mineralocorticoid antagonist (MRAs) suffer from adverse feminizing system (for spironolactone) and hyperkalemia (a class effect) that their use or becomes an indication for their withdrawal. Moreover, even under clinical trial conditions, there is a high rate of non-adherence to antihypertensive treatment revealed by in patients with uncontrolled/drug resistant hypertension. The number of patients with uncontrolled (drug resistant hypertension, and the problems of their management, have grown considerably with the publication of the SPRINT trial and its conclusion that the Systolic Blood Pressure (SBP) goal should be 120 rather than 140 mmHg for hypertension with cardiovascular risk. Thus, there is a considerable and growing unmet need for a safer and more effective and better tolerated MRA regimen to treat these patients.

A combined therapy with torsemide ER and Eplerenone addresses this unmet need from several viewpoints.

Providing Eplerenone as an ER formulation should enhance its effectiveness since its half-life of 4-6 hours is marginal for once daily dosing. This would reduce the need for the poorly tolerated spironolactone.

The once daily combination dosage should enhance drug compliance. This is a major problem in this population.

The combination should provide additive anti-hypertensive effectiveness yet subtractive (balanced) effects on serum potassium. This should extend MRA therapy to the many patients developing, as at risk for hyperkalemia.

The great effectiveness should bring more patients to goal at the new lower BP levels. This should reduce cardiovascular and cerebrovascular complications.

This may place patients with CKD and diabetes mellitus (DM) who are at special need for MRA therapy, yet at special risk of hyperkalemia, within a group that could receive MRA therapy Torsemide, like furosemide and bumetanide, is a loop diuretic that inhibits the coupled reabsorption of Na+/K+/2Cl− via the luminal Na—K—Cl cotransporter-2 (NKCC2) in the thick ascending limb of the loop of Henle. Since about 22% of filtered Na+ is reabsorbed by the cotransporter, torsemide is a highly potent natriuretic agent. It sharply increases the excretion of Na+, Cl− and fluid along with a K+ excretion at higher doses.

However, the abrupt natriuresis with loop diuretic is followed by a period of decrease Na+ excretion and repeat doses lead to diminishing response. This restricts the therapeutic effectiveness of all current loop diuretics in ridding the body of excessive Na+ and fluid. Five factors have been identified that account for these unfavorable effects. First, is increased reabsorption of Na+ by a downstream nephron site in the distal tubule and collecting duct. Second, is release of renin and angiotensin that stimulate aldosterone and thereby reabsorption of Na+ in the collecting duct. Third, is the generation of a metabolic alkalosis from preferential excretion of Cl− with relative retention of HCO3− that impairs the inhibition of NKCC2 by loop diuretics. Fourth, is a fall in glomerulus filtration rate (GFR) of about 20% seen with loop diuretic administration. Fifth, is the very short duration of action of 3-5 hours of all loop diuretics that leave the renal tubules free to reabsorb NaCl during the majority of the day, even when the diuretic is given twice daily.

Eplerenone, like spironolactone and its metabolites binds to, and inhibits, the mineralocorticoid receptor (MR) that is predominantly expressed in the collecting duct, where 1-2% of filtered Na+ is normally reabsorbed. Activation of MR by aldosterone decreases the degradation of the beta subunit of the luminal sodium channel (ENaC) that enhances cellular Na+ entry and thereby the lumen-negative trans-epithelial electrical potential that facilitates the secretion of K+ and H+ into tubular fluid. The result of MR blockade is a gradual and modest increase in Na+ excretion accompanied by a decreased excretion of K+ and H+ with the propensity to cause hyperkalemia and metabolic acidosis. The efficacy of a MR antagonist (MRA) is increased during condition of hyperaldosteronism including edematous states and patients with drug resistant hypertension, as demonstrated in PATHWAY-2 trial. Although shown to have considerable benefits in patients with some categories of heart failure or renal disease, the clinical effectiveness of MRAs has been limited by adverse effects. These include feminizing effects that are limited to spironolactone and hyperkalemia, especially in patients receiving ACEI/ARB therapy or with CKD or DM that is a class effect. This precludes the use of MRAs in many patients who might otherwise benefit.

Additive and/or synergistic actions of extended release torsemide and Eplerenone in patients with hypertension are:

First, Eplerenone enhances the NaCl loss with torsemide ER by several mechanisms:

Blocking the effect of angiotensin dependent aldosterone secretion and thereby reducing post-diuretic Na+ retention by blocking aldosterone-dependent upregulated reabsorption in the collecting duct.

Correcting metabolic alkalosis

Second, Torsemide ER enhances the NaCl loss with Eplerenone and reduce its principal adverse effect of hyperkalemia by several mechanisms—

Increasing the delivery of Na+ to the site of MR action in the collecting duct, thereby making Eplerenone more effective in ridding the body of Na+ and fluid Increasing the excretion of K+ at higher doses, thereby reducing K+ retention and hyperkalemia Both torsemide and Eplerenone are effective anti-hypertensive drugs. Although both likely reduce BP in part by reduction in body fluid volume, they act on different segments of the nephron and therefore should have additive actions.

Torsemide is reported not to prevent aldosterone-mediated MR activation in cardiomyocytes and thereby should not impair the cellular action of Eplerenone. Both torsemide and spironolactone prevent cardiac remodeling in dilated cardiomyopathy.

Thus, a combination of extended release torsemide and Eplerenone exert s beneficial additive effects in reducing body fluid and blood pressure, and beneficial effects in limiting the adverse effects of hyperkalemia often encountered with MRA therapy.

The principal benefits of the torsemide ER and Eplerenone combination are in the management of patients with uncontrolled hypertension who have developed hyperkalemia on spironolactone therapy. These patients have received a diuretic plus two additional anti-hypertensive drugs (often an ACEI or ARB plus a CCB) but have not achieved a BP to meet the JNC8 target level recommendations by the ACC/ASH/AHA expert group.

This combination can further be used to aid with the severity of obstructive sleep apnea and arterial stiffness in patients with resistant arterial hypertension. The extended release torsemide would aid with complications related to secondary hypertension, chronic kidney failure and arterial stiffness.

Treatment of arterial hypertension in the course of OSA should include the simultaneous use of several antihypertensive drugs with different mechanisms of action, including a diuretic and, optimally, a drug that inhibits the effect of aldosterone. An inhibitor of aldosterone receptors may lower blood pressure and reduce apnea counts at night. The combination of torsemide in a formulation comprising wet granulation would be a novel and optimal delivery vehicle in a suggested mechanism of action.

Further, certain particle sizes of HPMC and formulations are provided herein which would achieve desired release profiles. Obstructive sleep apnea is one of the most common causes of reversible increases in blood pressure and a clinically important factor predisposing to the development of hypertension refractory to treatment.

Continued antihypertensive treatments such as torsemide coupled with the use of aldosterone receptor antagonists, a SGLT inhibitor, and a sympatholytic agent or an anxiolytic agent would provide for a method of treatment of obstructive sleep apnea.

A method of treating hyperuricemia is also presented herein wherein a daily dose of extended or instant release torsemide is combined with other drug products. The drug products may be an SGLT inhibitor, a sympatholytic agent, or an anxiolytic agent.

Certain particle sizes of HPMC and formulations are provided herein which would achieve desired release profiles. to treat brain disorders such as Autism spectrum disorder, the other drug products could further include NKCC inhibitors, or N-Methyl-D-Aspartate (NMDA) receptor antagonists. These combinations will also be used to treat brain disorders including schizophrenia, Parkinson disease, Rett syndrome, and neuropathic pain.

In another embodiment, the other drug products could be an aldosterone receptor antagonist. The other drug products may be coupled with torsemide in a singular fashion or be combined alongside a variety of release profiles. HPMC weight, particle size, and high-density microcrystalline cellulose, as well as lactose monohydrate can be manipulated to alter delivery.

In the drawings and specification, there have been disclosed typical preferred embodiments of the invention and, although specific terms are employed, they are used in a generic and descriptive sense only and not for purposes of limitation, the scope of the invention being set forth in the following claims.

A method for treating a patient clinically diagnosed for chronic congestive heart failure, chronic kidney disease, hypertension and diabetes individually or any combinations thereof, the method comprising the steps of determining serum and urinary creatinine levels to estimate glomerular filtration rate, diabetes by obtaining a blood glucose sample from the patient; and performing or having performed an assay on the sample to determine if the patient has diabetes; and measuring ejection fraction or serum brain natriuretic peptide (BNP) levels to assess heart failure; and if the patient has heart failure and diabetes with or without chronic kidney disease, then orally administering torsemide ER and SGLT inhibitor combination to the patient wherein torsemide amount is 5 mg to 200 mg per day and SGLT inhibitor amount is 1 mg-100 mg per day; and if the patient has uncontrolled with or without heart failure, then orally administering torsemide and aldosterone receptor antagonist combination to the patient wherein torsemide amount is 5 mg to 200 mg per day and aldosterone receptor antagonist amount is 1 mg-200 mg per day.

A method for treating a patient clinically diagnosed with sleep apnea, the method comprising the administration of a daily dose of 5-200 mg torsemide or a pharmaceutically acceptable salt thereof, and at least one other drug product such as an aldosterone receptor antagonist (e.g., spironolactone or eplerenone), sodium glucose linked transporter (SGLT) inhibitor, a sympatholytic agent or an anxiolytic agent. The at least one other drug product could also be used as a combination of agents listed above. In an embodiment, the torsemide formulation could further be used with HPMC formulations and particle sizes as previously recited. Lactose monohydrate would also be used in similar ranges. In another embodiment, the other drug products may be formulated in an extended release or immediate release form.

A method for treating a patient clinically diagnosed with hyperuricemia, the method comprising the administration of a daily dose of 5-200 mg torsemide or a pharmaceutically acceptable salt thereof, and at least one other drug product such as an aldosterone receptor antagonist (e.g., spironolactone or eplerenone), sodium glucose linked transporter (SGLT) inhibitor, a sympatholytic agent or an anxiolytic agent. The at least one other drug product could also be used as a combination of agents listed above. In an embodiment, the torsemide formulation could further be used with HPMC formulations and particle sizes as previously recited. Lactose monohydrate would also be used in similar ranges. In another embodiment, the other drug products may be formulated in an extended release or immediate release form.

A method for treating a patient clinically diagnosed with Autism Spectrum Disorder, the method comprising the administration of a daily dose of 5-200 mg torsemide or a pharmaceutically acceptable salt thereof, and at least one other drug product such as an aldosterone receptor antagonist (e.g., spironolactone or eplerenone), sodium glucose linked transporter (SGLT) inhibitor, a sympatholytic agent or an anxiolytic agent. The at least one other drug product could also be used as a combination of agents listed above. In an embodiment, the torsemide formulation could further be used with HPMC formulations and particle sizes as previously recited. Lactose monohydrate would also be used in similar ranges. In another embodiment, the other drug products may be formulated in an extended release or immediate release form.

A method for treating a patient clinically diagnosed with a brain disorder, the method comprising the administration of a daily dose of 5-200 mg torsemide or a pharmaceutically acceptable salt thereof, and at least one other drug product such as an aldosterone receptor antagonist (e.g., spironolactone or eplerenone), sodium glucose linked transporter (SGLT) inhibitor, a sympatholytic agent, an anxiolytic agent, or N-Methyl-D-Aspartate (NMDA) receptor antagonist. The at least one other drug product could also be used as a combination of agents listed above. In an embodiment, the torsemide formulation could further be used with HPMC formulations and particle sizes as previously recited. Lactose monohydrate would also be used in similar ranges. In another embodiment, the other drug products may be formulated in an extended release or immediate release form.

In an embodiment, the brain disorder to be treated can be Autism ASD, schizophrenia, Parkinson disease, Rett Syndrome, or neuropathic pain. It is an object of the present invention that the disclosed compounds and formulations can be used to treat a patient who is clinically diagnosed with one or more than one disorders.

Sleep Disorders in Heart Failure (HF)

HF is characterized by a disproportionately high prevalence of sleep disordered breathing (SDB), sleep deprivation, and fragmented sleep. Insufficient sleep can negatively affect quality of life as well as cognitive processes and memory, which may in turn reduce HF treatment adherence. Given the importance of sound sleep on daily functioning and overall health, the high prevalence of sleep disorders in HF is concerning, and treating sleep disorders in the context of HF syndrome is becoming a clinical priority.

Sleep Disordered Breathing

Sleep Apnea Syndrome is perhaps the most clinically significant sleep disorder in HF, affecting approximately 50% of patients. Traditionally, sleep apnea is defined as the absence of airflow of ≥90% for ≥10 seconds; a hypopnea is defined as a decrement in airflow of ≥50% but <90% for ≥10 seconds. Overall severity of sleep apnea is assessed via the Apnea-Hypopnea Index (AHI), which is a summation of the number of apneas and hypopneas per hour of sleep. Generally, an AHI <5 indicates normal, 5-15 mild apnea, >15-30 moderate apnea, and >30 severe apnea.

Sleep apnea is classified according to two primary mechanisms: obstructive sleep apnea (OSA) and central sleep apnea (CSA). OSA is caused by a blockage of the airway, usually when the soft tissue in the rear of the throat collapses and closes during sleep. CSA is believed to result from the slower circulation of blood in HF and a consequent unmasking of the apneic threshold due to the decrease in the blood's partial pressure of carbon dioxide ($PaCO_2$), resulting in cessation of breathing. OSA is a known risk factor for HF; whereas, CSA is most often a consequence of HF. Approximately 35% of HF patients have OSA, compared to approximately 3% to 7% in the general population. Prevalence of CSA in HF patients is 35% to 66%; whereas, prevalence of CSA in the general population is uncommon. Longitudinal studies indicate that untreated OSA and/or CSA in HF can increase risk of mortality. HF patients often have a combination of OSA and CSA.

Currently continuous positive airway pressure (CPAP) is the recommended treatment for OSA, including HF patients. CPAP has been found to improve left ventricular ejection fraction (LVEF), and although limited, there is evidence to suggest that CPAP may reduce risk of mortality and hospitalization in HF. Randomized control trials (RTCs) of therapy for CSA in HF have not established a significant benefit with respect to hospitalization or mortality, and thus, there is no consensus on an optimal treatment strategy. Optimal treatment of HF, using angiotensin-converting enzyme inhibition and β-blockers, has been associated with alleviation of CSA. In addition, theophylline, nocturnal oxygen supplemental, automatic positive airway pressure (APAP) with adaptive servo-ventilation have shown promise in reducing CSA.

Insomnia and Poor Sleep Architecture

Difficulty initiating or maintaining sleep, waking up too early, and non-restorative sleep are common complaints among HF patients, and are also subtypes of insomnia. In addition to apnea, sleep deprivation may be exacerbated by elevation in sympathetic nervous system activity, which is common to HF. Onset or exacerbation of insomnia may also be related to mood disorders and psychological stress, which often accompany chronic disease. ACC/AHA guidelines have identified lack of or poor sleep as a barrier to self-care and treatment adherence in HF patients, providing yet another route to increased risk of morbidity and mortality. Due to the lack of randomized controlled trials, assessing treatment of comorbid insomnia, it remains uncertain if treatments for primary insomnia are effective in HF. Precise treatment of co-morbid insomnia depends on the cause, but in the absence of a known cause, rameleteon has been used. Pharmacological therapies for sleep should have minimal drug interactions because optimal management of HF already involves a complex medication regimen. Also, elimination times for medications may be prolonged in HF, which may result in increased risk for residual daytime effects for sleep agents with longer half-lives. Thus, non-pharmacologic therapy may be optimal for HF patients with co-morbid insomnia, including sleep hygiene education, cognitive therapy, relaxation therapy, stimulus control therapy, and sleep restriction therapy.

Standard Pharmacological Therapies for HF and Sleep

Although frequently overlooked, standard pharmacological therapies for treating HF may also contribute to sleep problems. ACC/AHA guidelines state that most patients with HF with systolic dysfunction should be routinely managed with a combination of three classes of drugs: angiotensin converting enzyme inhibitors (ACEIs) or an angiotensin receptor blockers (ARBs), diuretics, and β-blockers. Proper use of these medications has dramatically improved HF morbidity and mortality rates. ACEI, ARBs and β-blockers are often used in patients with HF with a preserved ejection fraction (HFpEF); however, there is less data to indicate that their use reduces morbidity and mortality due to HF. Much remains unknown about the extent to which these agents affect sleep in HF patients, who often already have existing sleep disorders.

Aldosterone Receptor Antagonists

Aldosterone acts on the distal nephron resulting in conservation of sodium, secretion of potassium, increased water retention, and increased blood pressure. High levels of aldosterone have been associated with anatomical changes in cardiac myocytes, endothelial dysfunction, and cardiovascular fibrosis and remodeling. Given the deleterious effects of high levels of aldosterone, HF patients may require long-term suppression via aldosterone receptor antagonists (e.g., spironolactone and eplerenone). Spironolactone is the most widely used, and in low doses, in addition to ACEI therapy, has been shown to reduce morality.

Effects of Aldosterone Receptor Antagonists on Sleep

Data suggests that aldosterone excess may contribute to OSA severity. The proposed mechanism for this association is that chronic aldosterone-induced fluid retention causes peripharyngeal edema, which obstructs the upper airway and may be exacerbated by supine position during sleep. A preliminary study assessing 12 resistant hypertensive patients with OSA showed that spironolactone treatment was associated with reductions in AHI (39.8±19.5 vs. 22.0±6.8 events/h; $p<0.05$) and the hypoxic index (13.6±10.8 vs. 6.7±6.6 events/h; $p<0.05$).

In our own laboratory, we utilized polysomnography to examine the potential effects of ACEIs, ARBs and aldosterone receptor antagonists (e.g., spironolactone or eplerenone) on sleep architecture and SDB in 67 NYHA classes II and III HF patients [mean age 55.6 years (±13.4)]. Seventy-seven percent (n=52) of patients were taking an ACEI, 16.4% (n=11) were taking an ARB, and 40.3% (n=27) were taking an aldosterone receptor antagonist. Using linear regression analysis, adjusting for age, sex and BMI, we found that aldosterone receptor antagonists (e.g., spironolactone and eplerenone) were associated with patients having fewer awakenings following sleep onset ($\beta=-0.277$, $p\leq0.03$) and spending less time in stage 1 sleep ($\beta=-0.240$, $p\leq0.05$). Although not statistically significant, patients taking aldosterone receptor antagonists (e.g., spironolactone or eplerenone) also spent more time in Stage 2 sleep, SWS, and REM sleep.

Loop Diuretics

Loop diuretics are the primary method of treating fluid retention in HF, producing symptomatic benefits more rapidly than any other drug. Diuretics interfere with the sodium retention of HF by inhibiting the reabsorption of sodium or chloride at specific sites in the renal tubules. Loop diuretics are usually the preferred course of treatment because of their efficacy in increasing sodium excretion up to 20% to 25% of the filtered load of sodium, enhancing free water clearance and maintaining their efficacy even in cases of severe renal impairment.

Effects of Loop Diuretics on Sleep

Research of the effects of loop diuretics on sleep is scarce; however, diuretic administration is often associated with nocturia, which may result in sleep fragmentation. On the other hand, preliminary work indicates that administration of loop diuretics may improve OSA by reducing peripharyngeal edema. Studies examined if intensive unloading with IV administration of furosemide (20 mg bid for 3 days), co-administered with spironolactone (100 mg), improved OSA in 15 patients with severe OSA, systemic hypertension, and diastolic HF. Results indicated improvements in AHI, oropharyngeal junction (OPJ) area, and blood pressure, as well as a decrease in body weight.

Hyperuricemia is a relatively common finding in patients treated with a loop or thiazide diuretic and may, over a period of time, contribute to onset of gouty arthritis or exasperation of established gout. Diuretics reduce urate excretion by both directly and indirectly increasing urate reabsorption and decreasing urate secretion and these effects are dose dependent. If diuretic-induced gout occurs, it is usually treated with a urate-lowering drug such as allopurinol.

The proximal tubule is the major site of urate handling; both secretion and reabsorption occur in this segment, with the net effect being reabsorption of most of the filtered urate. Urate enters the proximal tubular cell from peritubular capillary blood through organic anion transporters 1 and 3 (OAT1 and OAT3) located on the basolateral membrane, and is secreted from the cell into the tubular fluid through solute carrier (SLC) family members SLC17A1 and SLC17A3, multidrug resistance protein 4 (MRP4), and ATP-binding cassette G2 (ABCG2) located on the luminal membrane. Urate reabsorption from the tubular fluid into the cell is mediated by urate transporter 1 (URAT1), OAT4, and OAT10, located on the luminal membrane, and from the cell back to the peritubular capillary blood through glucose transporter 9 (GLUT9) located on the basolateral membrane. Loop and thiazide diuretics decrease urate excretion by increasing net urate reabsorption; this can occur either by enhanced reabsorption or by reduced secretion.

Hyperuricemia is closely linked to diabetes, since insulin resistance is correlated with serum uric acid (SUA) levels. Insulin has been suggested to increase uric acid reabsorption in the proximal tubule. when diabetes progresses to the stage of glycosuria, the serum uric acid level begins to decrease. These mechanisms have been proposed as an effect of glucose on uric acid handling in the proximal tubule. This phenomenon is similar to the SUA-lowering effect of SGLT inhibitors.

We have shown that loop diuretic-induced hyperuricemia can be treated with extended release torsemide used in combination with a SGLT inhibitor.

The regulation of the intracellular neuronal chloride levels determines the efficacy of GABAergic inhibition. High chloride levels can reverse the polarity of GABA actions from inhibition to excitation. In contrast to immature neurons that have high chloride levels, adult ones have usually low chloride levels and inhibitory actions of GABA. However, high chloride levels and excitatory actions of GABA are produced by a wide range of disorders and insults including seizures, brain trauma, spinal cord lesions, cerebrovascular infarcts or chronic pain. As GABAergic networks have essential roles in the generation of behaviorally relevant oscillations, a polarity shift of the actions of GABA will impact sensory and integrative properties of the brain and exert major deleterious effects. These observations have raised considerable interest in the development of pharmacological treatments that restore physiological chloride levels and GABAergic inhibition in pathological conditions. In experimental conditions, the high affinity specific NKCC1 chloride-importer inhibitor torsemide can reduce chloride levels, can restore GABAergic inhibition and attenuates the severity of electrical or behavioral manifestations in many pathological conditions. Torsemide is therefore a good candidate to test clinically.

Autism Spectrum Disorder (ASD) and Other Brain Disorders

Neocortical neurons have elevated chloride levels and excitatory GABA. Studies have shown that loop diuretic attenuate the severity of ASD in 5-11 years old children. Similar observations were made in an open-label trial pilot study in adolescents with ASD, where use of loop diuretic improved emotion recognition and activation of brain regions involved in social and emotional perception in functional magnetic resonance imaging and neuropsychological testing.

The effect of chloride ions has also been reported in regard to other diseases such as schizophrenia, Parkinson's Disease, Rett syndrome. In all of these cases, blocking the chloride ion channels has improved disease symptoms. Since loop diuretics can block NCCK, they are good candidates for the treatment of these diseases. More specifically, since torsemide seems to cross blood brain (BBB) barrier better than any other loop diuretics, and the BBB crossing a duration/exposure dependent, extended release torsemide is the best candidate to treat these diseases.

TABLE 8

Prediction of Blood Brain Barrier Permeability

| | Furosemide | Bumetanide | Torsemide | Azosemide | Ethacrynic acid | Range |
|---|---|---|---|---|---|---|
| MW | 331 | 364 | 348 | 371 | 303 | <500 |
| tPSA | 123 | 119 | 100 | 127 | 64 | <100 |
| HD | 3 | 3 | 3 | 3 | 1 | <3 |
| cLogP | 1.9 | 3.37 | 3.21 | 1.36 | 3.44 | 2--5 |

Dose equivalence: 1 mg bumetanide = 20 mg torsemide = 40/60 mg furosemide = 50 mg ethacrynic acid = 60 mg azosemide

| | $IC_{50}$ (μM) | | |
|---|---|---|---|
| | hNKCC1a | hNKCC1b | NKCC2 |
| Azodemide | 0.25 | 0.21 | 3.1 |
| Bumatenide | 0.95 | 0.84 | 0.25 |
| Furosemide | 5.2 | 5.8 | 5.1 |

TABLE 8-continued

Prediction of Blood Brain Barrier Permeability

| | | | |
|---|---|---|---|
| Torsemide | 6.2 | 8.2 | 0.3 |
| Ethacrynic acid | 1678 | 3071 | 5.1 |

TABLE 9

Dosage Formulations and Selectivity for Torsemide and Bumetanide

| Parameter | Torsemide | Dapagliflozin (Day 1-7) | Bumetanide (Day 1-7) | Dapagliflozin and Bumetanide (Day 1-7) | Dapagliflozin and Bumetanide (Day 8-14) |
|---|---|---|---|---|---|
| Volume, mL-wk$^{-1}$ | | 16082 ± 2146 | 16445 ± 1612 | 20033 ± 1983 (P < 0.05 vs dapagliflozin or bumetanide alone) | 16272 ± 1567 |
| Glucose, g-wk$^{-1}$ | | 239 ± 20 | 0.3 ± 0.06 | 188 ± 20 (P < 0.05 vs bumetanide) | 150 ± 19 (P < 0.05 vs bumetanide) |
| Na$^+$, mmol-wk$^{-1}$ | | 625 ± 15 | 669 ± 46 | 723 ± 28 (P < 0.05 vs dapagliflozin alone) | 742 ± 19 (P < 0.05 vs dapagliflozin or bumetande alone) |
| K$^+$, mmol-wk$^{-1}$ | | 415 ± 24 | 454 ± 32 | 514 ± 35 (P < 0.05 vs dapagliflozin alone) | 442 ± 28 |
| Urate, mg-wk$^{-1}$ | | 3382 ± 187 | 2249 ± 160 | 3163 ± 211 (P < 0.05 vs bumetanide alone) | 2598 ± 160 |
| Ca$^{++}$, mg-wk$^{-1}$ | | 597 ± 76 | 667 ± 54 | 646 ± 33 | 707 ± 40 |
| Mg$^{++}$, mg-wk$^{-1}$ | | 548 ± 37 | 613 ± 48 | 611 ± 42 | 552 ± 52 |

TABLE 10

Serum or Plasma Values with Diuretic Administration of Torsemide and Bumetanide

| Parameter | Before (Day −1) | Dapagliflozin (Day 8) | Before (Day −1) | Bumetanide (Day 8) | Before (Day −1) | Dapagliflozin + Bumetanide (Day 8) | Dapagliflozin + Bumetanide (Day 14) |
|---|---|---|---|---|---|---|---|
| S$_{Na}$, mmol-L$^{-1}$ | 137.9 ± 0.5 | 138.1 ± 0.4 | 137.7 ± 0.3 | 137.8 ± 0.3 | 138.1 ± 0.4 | 137.1 ± 0.4* | 138.3 ± 0.5 |
| S$_{osm}$, mOsmol-L$^{-1}$ | 283.5 ± 0.8 | 285.4 ± 0.7* | 283.9 ± 1.0 | 285.4 ± 0.9 | 284.4 ± 0.9 | 283.3 ± 0.9 | 284.3 ± 1.0 |
| Serum glucose, mg-dL$^{-1}$ | 86.3 ± 2.0 | 82.3 ± 2.0† | 88.4 ± 2.2 | 85.5 ± 1.8* | 87.2 ± 1.4 | 82.4 ± 2.5* | 84.0 ± 1.7* |
| S$_K$, mmol-L$^{-1}$ | 4.5 ± 0.09 | 4.4 ± 0.08 | 4.4 ± 0.07 | 4.1 ± 0.09* | 4.6 ± 0.1 | 4.1 ± 0.07‡ | 4.0 ± 0.008‡ |
| Surate, mmol-L$^{-1}$ | 5.5 ± 0.3 | 3.5 ± 0.2‡ | 5.9 ± 0.3 | 6.1 ± 0.4* | 5.4 ± 0.4 | 4.2 ± 0.3† | 4.3 ± 0.3* |
| S$_{Cr}$, mg-dL$^{-1}$ | 0.9 ± 0.05 | 1.0 ± 0.04‡ | 0.9 ± 0.04 | 1.0 ± 0.05* | 0.9 ± 0.05 | 1.0 ± 0.05‡ | 1.0 ± 0.05‡ |
| Plasma renin activity, ng-mL$^{-1}$-h$^{-1}$ | 3.4 ± 0.7 | 3.4 ± 0.9 | 3.6 ± 0.8 | 7.8 ± 1.8* | 5.6 ± 1.2 | 9.8 ± 2.0 | 6.2 ± 1.1 |

The parameters which considered in the appropriate dosage levels will take into determining creatinine clearance, calcium and magnesium excretion, daily urate excretion, potassium and serum urate concentration as well as renal urate clearance of glucose, sodium and potassium. Once these factors have been considered by obtaining samples from the patient and performing an assay on the sample, dosage formulations may be prescribed and adjusted.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. An oral dosage formulation manufactured by wet granulation comprising: spironolactone or a pharmaceutically acceptable salt thereof as an active ingredient; 27 wt % to 34 wt % of hydroxypropyl methyl cellulose; 25 wt % to 53 wt % of high-density microcrystalline cellulose of nominal particle size of about 100 micrometers; and 6.5 wt % to 8 wt % of lactose monohydrate.

2. The formulation of claim 1, wherein a weight per dosage of spironolactone is between 15-45 mg.

3. The formulation of claim 1, wherein a weight per dosage of spironolactone is 15 mg.

4. The formulation of claim 1, wherein the formulation is used for the treatment of heart failure with preserved ejection fraction.

5. The formulation of claim 2, wherein the formulation is used for the treatment of heart failure with preserved ejection fraction.

6. The formulation of claim 3, wherein the formulation is used for the treatment of heart failure with preserved ejection fraction.

7. The formulation of claim 1, wherein the formulation is used for the treatment of uncontrolled hypertension.

8. The formulation of claim 2, wherein the formulation is used for the treatment of uncontrolled hypertension.

9. The formulation of claim 3, wherein the formulation is used for the treatment of uncontrolled hypertension.

* * * * *